US011707327B2

(12) United States Patent
Schmidt et al.

(10) Patent No.: US 11,707,327 B2
(45) Date of Patent: Jul. 25, 2023

(54) SYSTEMS AND METHODS FOR MODELING SPINES AND TREATING SPINES BASED ON SPINE MODELS

(71) Applicant: K2M, Inc., Leesburg, VA (US)

(72) Inventors: John Schmidt, Bluemont, VA (US); Margaret Redford, Isle of Palms, SC (US); Jennifer McCool, Boyce, VA (US); Anthony Young, Annandale, VA (US); Noah Q. Johnson, Leesburg, VA (US); Kylie Pleakis, Bradford, PA (US)

(73) Assignee: K2M, Inc., Leesburg, VA (US)

( * ) Notice: Subject to any disclaimer, the term of this patent is extended or adjusted under 35 U.S.C. 154(b) by 50 days.

(21) Appl. No.: 17/529,993

(22) Filed: Nov. 18, 2021

(65) Prior Publication Data

US 2022/0151699 A1 May 19, 2022

Related U.S. Application Data

(63) Continuation of application No. 16/630,752, filed as application No. PCT/US2018/041831 on Jul. 12, (Continued)

(51) Int. Cl.
*A61B 34/10* (2016.01)
*G06T 7/00* (2017.01)
*G06T 19/20* (2011.01)

(52) U.S. Cl.
CPC .......... *A61B 34/10* (2016.02); *G06T 7/0012* (2013.01); *G06T 19/20* (2013.01);
(Continued)

(58) Field of Classification Search
CPC ......... G06T 19/00; G06T 17/20; G06T 17/00; G06T 15/10; G06T 15/00
See application file for complete search history.

(56) References Cited

U.S. PATENT DOCUMENTS 7,657,072 B2   2/2010  Periaswamy et al.
8,527,244 B2   9/2013  Shin
(Continued)

FOREIGN PATENT DOCUMENTS

WO     9959106 A1    11/1999
WO   2017027873 A1    2/2017

OTHER PUBLICATIONS

Huynh KT, Gibson I, Gao Z. Development of a detailed human spine model with haptic interface. InHaptics Rendering and Applications 2012. InTech. Uploaded by Ian Gibson May 21, 2014, 31 pages.
(Continued)

*Primary Examiner* — Todd Buttram
(74) *Attorney, Agent, or Firm* — Howard & Howard Attorneys PLLC

(57) ABSTRACT

Disclosed are systems and methods for rapid generation of simulations of a patient's spinal morphology that enable pre-operative viewing of a patient's condition and to assist surgeons in determining the best corrective procedure and with any of the selection, augmentation or manufacture of spinal devices based on the patient specific simulated condition. The simulation is generated by morphing a generic spine model with a three-dimensional curve representation of the patient's particular spinal morphology derived from existing images of the patient's condition.

24 Claims, 36 Drawing Sheets

Related U.S. Application Data 2018, now Pat. No. 11,207,135, which is a continuation of application No. 15/648,086, filed on Jul. 12, 2017, now Pat. No. 11,000,334.

(60) Provisional application No. 62/666,305, filed on May 3, 2018, provisional application No. 62/565,586, filed on Sep. 29, 2017.

(52) U.S. Cl.
CPC .............. *A61B 2034/105* (2016.02); *G06T 2207/10116* (2013.01); *G06T 2207/30012* (2013.01); *G06T 2210/41* (2013.01); *G06T 2219/2016* (2013.01)

(56) References Cited

U.S. PATENT DOCUMENTS

| | | | |
|---|---|---|---|
| 9,393,130 B2 | 7/2016 | Suddaby et al. | |
| 9,408,638 B2 | 8/2016 | Kroll et al. | |
| 9,561,004 B2 | 2/2017 | Forsberg | |
| 9,566,163 B2 | 2/2017 | Suddaby et al. | |
| 9,572,601 B2 | 2/2017 | Stenulson et al. | |
| 9,585,762 B2 | 3/2017 | Suddaby et al. | |
| 10,874,460 B2 | 12/2020 | Schmidt et al. | |
| 10,892,058 B2 | 1/2021 | Schmidt et al. | |
| 10,987,169 B2 | 4/2021 | Turner et al. | |
| 11,000,334 B1 | 5/2021 | Young et al. | |
| 11,207,135 B2 * | 12/2021 | Schmidt | G16H 50/50 |
| 11,379,793 B2 | 7/2022 | Laster et al. | |
| 2009/0232378 A1 * | 9/2009 | Nakamura | G06T 7/337 382/131 |
| 2011/0295378 A1 | 12/2011 | Bojarski et al. | |
| 2014/0228860 A1 | 8/2014 | Steines et al. | |
| 2014/0323845 A1 * | 10/2014 | Forsberg | G06T 7/60 600/407 |
| 2015/0328004 A1 * | 11/2015 | Mafhouz | A61F 2/28 700/98 |
| 2016/0022323 A1 | 1/2016 | Seme et al. | |
| 2016/0166396 A1 | 6/2016 | McClintock | |
| 2016/0317187 A1 | 11/2016 | Seme et al. | |
| 2017/0228896 A1 | 8/2017 | Yu et al. | |
| 2020/0261156 A1 * | 8/2020 | Schmidt | G06T 19/20 |
| 2021/0118573 A1 | 4/2021 | Schmidt et al. | |
| 2022/0151699 A1 * | 5/2022 | Schmidt | A61B 5/4566 |

OTHER PUBLICATIONS

International Search Report for PCT/US2018/041831 dated Nov. 19, 2018.

International Search Report including Written Opinion for PCT/US2018/053743 dated Dec. 21, 2018.

\* cited by examiner

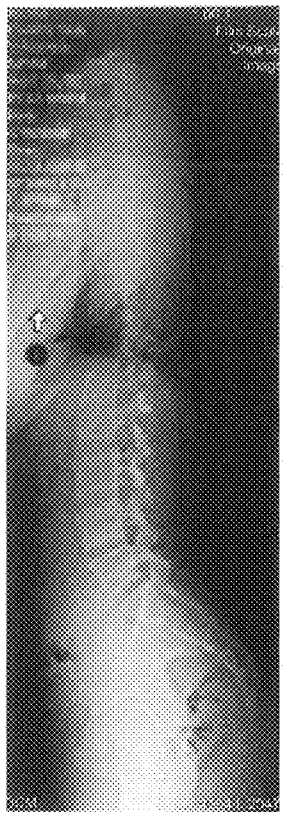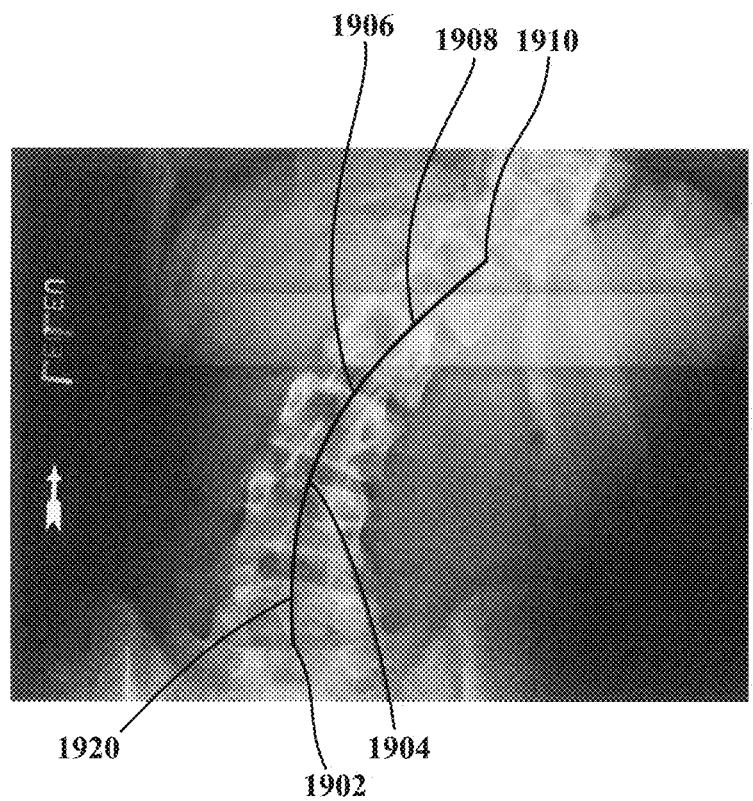
FIG. 19A                    FIG. 19B

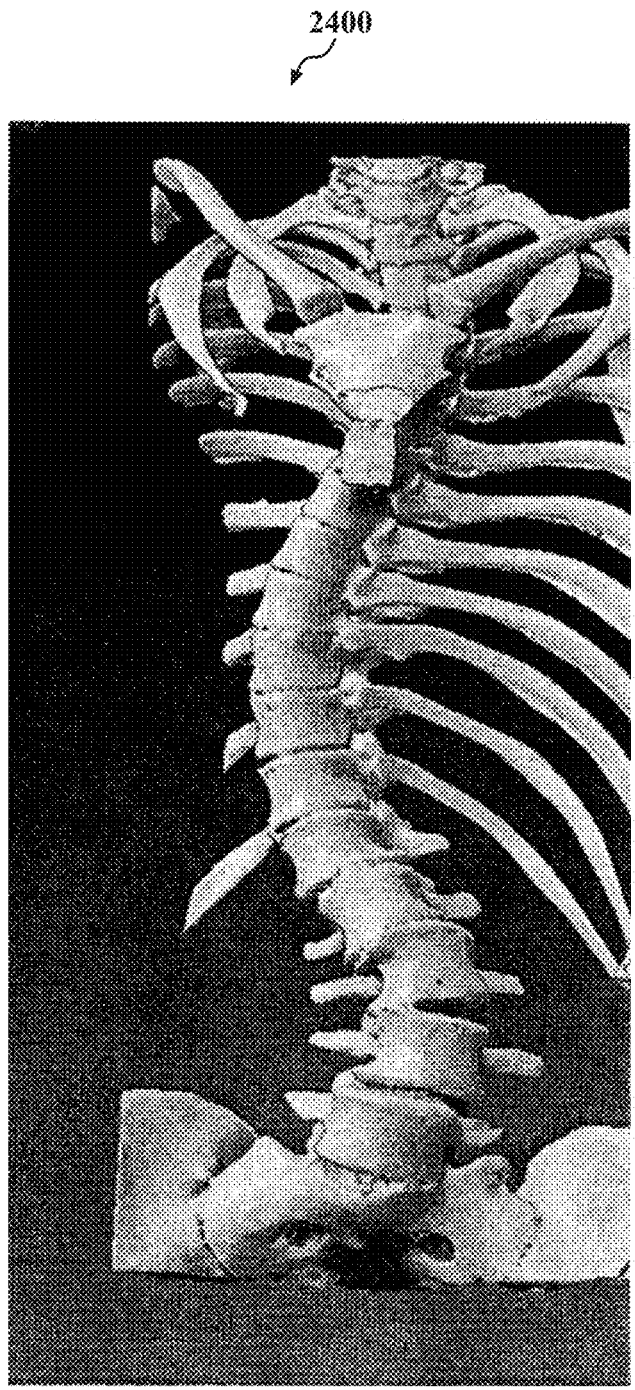
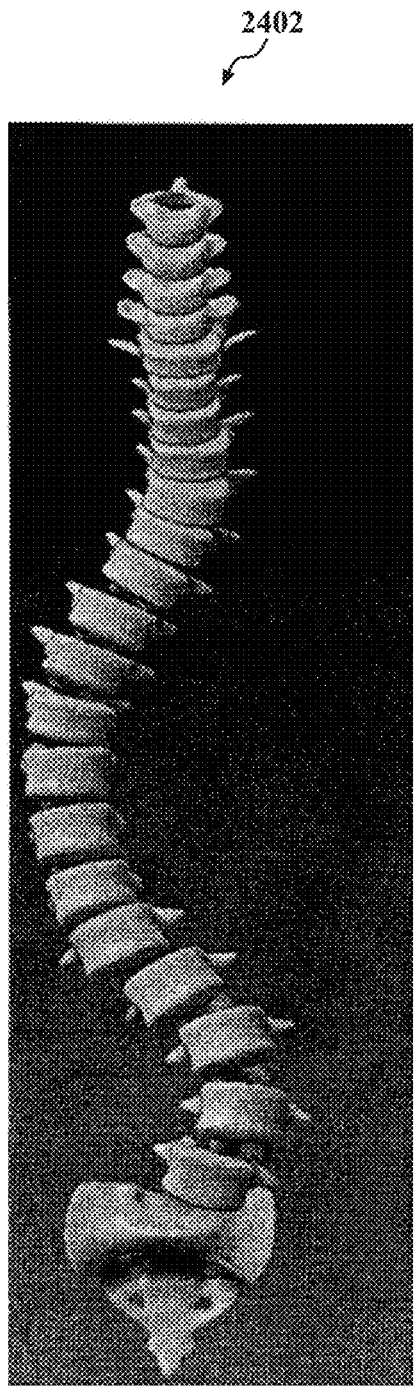
FIG. 24A
FIG. 24B

Gender: Male

Stiffness: Stiffness, Flexible

Distance Between
L1: 18.64 mm   L4:
L2: 18.86 mm   L5:
L3: 17.96 mm

Check All That Apply:
- ☐ Smoker
- ☐ Drinker
- ☐ Sedentary
- ☐ Obese

Choose Screw Material: Ti Alloy

Choose Screw Diameter: Screw Diameter: 4 mm

Choose Screw Len

Choose Rod Material: Ti Alloy

Choose Rod Length: Rod Length: 0

Choose Vertebral Bodies and Color

| | | |
|---|---|---|
| ☑ Left C1 | ☑ Right C1 | ○ Blue |
| ☐ Left C2 | ☐ Right C2 | ○ Pink |
| ☑ Left C3 | ☑ Right C3 | ● Red |
| ☐ Left C4 | ☐ Right C4 | ○ Black |

SYSTEMS AND METHODS FOR MODELING SPINES AND TREATING SPINES BASED ON SPINE MODELS

CROSS REFERENCE TO RELATED APPLICATIONS

This application is a Continuation of U.S. patent application Ser. No. 16/630,752, filed on Jan. 13, 2020; which is the national phase entry under 35 U.S.C. § 371 of International Patent Application No. PCT/US2018/041831, filed on Jul. 12, 2018. International Patent Application No. PCT/US2018/041831 is a Continuation of U.S. patent application Ser. No. 15/648,086, filed on Jul. 12, 2017, which granted as U.S. Pat. No. 11,000,334 on May 11, 2021. International Patent Application No. PCT/US2018/041831 also claims the benefit of U.S. Provisional Patent Application No. 62/565,586, filed on Sep. 29, 2017, and U.S. Provisional Patent Application No. 62/666,305, filed on May 3, 2018. The disclosures of each of these Applications are hereby incorporated by reference in their entirety.

BACKGROUND

1. Technical Field

This disclosure pertains generally to modeling aspects of the human skeleton, and, more particularly, to developing and using models of a spine and using other medical data relating to the spine to visualize and predict the results of a surgical procedure prior performing spinal surgery so as to result in a desired outcome, such as a balanced spine.

2. Discussion of Related Art

Today a wide-variety of surgical devices are being developed and used to perform various spinal surgical procedures. In many spine surgeries, surgical devices are used to correct a patient's spine so that the skull is oriented over or aligned with the pelvis. Specifically, the surgical devices and software are used to ensure that the vertebral bodies are in normal sagittal alignment so that there is a gradual transition of curvatures from cervical lordosis, to thoracic kyphosis, to lumber lordosis. Although such spinal surgery may result in normal sagittal alignment of the spine, the spine may not be properly aligned in either of the coronal or axial planes. One reason for only partial correction is that surgeons typically focus on spinal models that are described predominantly by angular data as measured among vertebral bodies in the sagittal plane, instead of actual spatial coordinates. Another reason for only partial correction is the failure to consider alignment of the spinal column in the coronal or axial planes as well as the sagittal plane. A further reason for only partial correction is the failure to use the alignment of the head with the center of the pelvis as an axis of reference in which to measure the deviation of the modeled spinal column in both the sagittal and coronal planes. A further reason for only partial correction is the inability to predict post-surgical results with even marginal accuracy. Computer modeling of a patient spine is currently available but requires prohibitively high computational resources.

Accordingly, a need exists for a systems and methods for constructing a three dimensional simulation of the curvature of a patient spine which accurately reflect the morphology of the patient.

A further need exists for a systems and methods for constructing a three dimensional simulation of the curvature of a patient spine which accurately reflect the morphology of the patient and can be generated quickly.

A still further need exists for a systems and methods for constructing a three dimensional simulation of the curvature of a patient spine which accurately reflect the morphology of the patient and which can be further modified based on data input from a surgeon to enable better prediction of post-surgical results.

An even further need exists for a systems and methods for constructing a three dimensional simulation of the curvature of a patient spine which accurately reflect the morphology of the patient and using other medical data relating to the spine to customize spinal devices and the methods of performing spinal surgery so as to result in a desired outcome, such as a balanced spine.

According to another aspect of the disclosure, prior attempts at modeling the morphology of an individual patient spine's to assist surgeons with both pre-operative and post-operative analysis has required very costly procedures which are then used to create either virtual or physical three-dimensional models of the patient's exact condition. Such modeling procedures are very resource intensive in terms of both time and cost typically taking hours of computing to render such models into a form usable by a surgeon and, accordingly, are not very practical for large-scale use by the medical community.

Accordingly, further need exists for a system and method which allows for rapid modeling of the morphology of the patient spine using x-ray data or CT scan data or MRI data which takes significantly less time and is significantly less computationally intensive.

SUMMARY

Disclosed are systems and methods for rapid generation of simulations of a patient's spinal morphology to enable pre-operative viewing of the patient's condition and to assist surgeons in determining the best corrective procedure and with any of the selection, augmentation or manufacture of spinal devices based on the patient specific simulated condition. The simulation is generated by morphing a generic normal spine model with a three-dimensional representation of the patient's spinal morphology derived from existing images of the patient's condition. Effectively, the disclosed methods emulate giving a normal spine model the patient's diseased condition. The resulting simulation of the patient's pathological and morphological condition enables the surgeon to observe the patient's condition preoperatively and to make better choices regarding corrective procedures, customized hardware and to better predict postoperative results.

According to one embodiment, in a first method for rapid generation of a simulated patient morphology, the center of vertebral body S1 endplate is used as a reference pivot point by which each point in every point cloud model of a VB is pivoted, translated, and rotated, as necessary, relative to the reference pivot point. In this method, after at least two different images in different planes normal to each other are obtained, a Central Vertebral Body Line is generated describing the curve of the patient spine in three-dimensional spatial coordinates. A model, e.g. a point map, of each vertebral body in a set of normal vertebral body models is retrieved and the end plates of vertebral bodies on one of the images are determined through either manual input or automated detection. The translation and tilt angles relative to the center point of each vertebral body are then calculated as well as the rotation vectors relative to the pivot point S1. Once the pivot point and the x,y,z coordinates of the points in a point cloud model are known, the point cloud model representing a vertebral body can be morphed in any order, e.g. translated, rotated, and then angled, or, angled, rotated, and then translated, etc., with the same result. Finally, the simulation may be rendered on a display.

According to another embodiment, a second method for rapid generation of a simulated patient morphology includes generation of a Central Vertebral Body Line similar to the previously described method. However, in this second method, the left/right/front/back edge end points of each VB are identified and a three-dimensional box of each of the VBs created. Because the box is defined by spatial coordinates, the dead center of each box may be determined, with the center point of a VB box serving as a reference pivot point. Every other point in the point cloud model for that individual VB is then pivoted, angled and translated relative to this reference pivot point. Because the data structure describing the three-dimensional box of each of VB inherently contains the respective spatial coordinates, rotation of the VB relative to a reference point, such a point S1, in the previously described method, is not required.

In the two methods outlined above, the data determining how the point cloud model of a VB will be rotated is determined differently. In the first method, the CVBL provides the translation data to move the VB point cloud model to the correct spatial locations, and further provides the angulation data to tilt the VB point cloud model so that its approximate center lie within the CVBL. In the first method, the reference point S1 is used to serve as the basis on which the rotation data, generated by measurement of the endplates and other characteristics of the VBs, is utilized. Such rotation data is used to rotate the translated and tilted the VB point cloud model into an orientation relative to the other VBs that simulates the patient's morphology. In the second method, the angulation data and the rotation data are determined by the center point of the vertebral body point cloud box which is initially assumed to lie on the CVBL, but, which after taking appropriate end plate and other measurements, may be determined to lie elsewhere. Once the center point of the VB box is known, the appropriate translation scaling factors are used to tilt and appropriately rotate the points comprising the VB point cloud model into appropriate orientation, without the need for an external reference point, such as S1, since the spatial coordinates describing the three-dimensional box of each of VB inherently define the rotation of the VB relative to its respective center point.

In another embodiment, a third method, all of the vectors associated with the point cloud of a VB are not calculated and morphed (translated, angled and rotated). Instead the central pivot point for each VB, which happens to run through the CVBL, generated as previously described, is identified. Next, a number of pixels, e.g. 5, both above and below a pivot point on the CVBL are examined and the slope in both the sagittal and coronal planes calculated. The calculated angles are then applied to the point cloud model of a VB and used to generate the image. This process is then repeated for each VB of interest within the original images from which the simulation was derived.

In one embodiment, the computer system for performing the above processes includes a communications interface, one or more processors coupled to the communications interface, and a memory coupled to the one or more processor and having stored thereon instructions which, when executed by the one or more processors, causes the one or more processors to acquire via the communications interface the first X-ray image of the spine in the first plane and the second X-ray image of the spine in the second plane from the server, store the first and second X-ray images in the memory, acquire a model of spine from the server, store the model of the spine in memory, determine a curve through vertebral bodies of the spine, determine coordinates of the spine by detecting the curve on the first X-ray image and the second X-ray image, construct a three-dimensional simulation of each vertebral body in the spine and morph the three-dimensional simulation into a realistic visualization of the patient morphology by translating, angulating and rotating the models of the vertebral bodies, perform predictive analysis on the three-dimensional simulation, and transmit via the communications interface for review and user input.

According to one aspect of the disclosure, a method for creating a visual simulation of a subject's condition, the method comprises: A) identifying at least one center point on each of a plurality anatomical structures in an image; B) deriving, from a plurality of identified center points, a linear representation of an arrangement of the anatomical structures, the linear representation comprising a set of three dimensional spatial coordinates including at least each of the identified center points of the anatomical structures; and C) arranging a corresponding virtual model of each of the plurality of anatomical structures such that a center point of each corresponding virtual model corresponds to the identified center point of the corresponding anatomical structure contained within the set of three dimensional spatial coordinates of the linear representation.

According to another aspect of the disclosure, a method for creating a visual simulation of a subject's condition, the method comprises: A) deriving, from a plurality of images of a subject, a linear representation of an arrangement of identified anatomical structures visible in the images, the linear representation comprising a set of three dimensional spatial coordinates corresponding to a center point of each of the identified anatomical structures; and B) arranging a virtual model of each of the plurality of identified anatomical structures according to the linear representation such that a center point of each virtual model corresponding to an identified anatomical structure is included in the set of three dimensional spatial coordinates, wherein arranging the virtual models further comprises one of pivoting the identified center point of each virtual model by an amount of identified angular displacement of the corresponding anatomical structure relative to the reference point in one of the images and rotating each virtual model by an amount of identified angular rotation of the corresponding anatomical structure relative to the reference point in one of the images.

According to still another aspect of the disclosure, a system for creating a visual simulation of a subject's condition, the system comprises a plurality of virtual models stored in computer accessible memory, each of the plurality of virtual models representing an anatomical structure and having an associated center point; an image processor unit, responsive to one or more images, operational to identify at least one center point on each of a plurality anatomical structures visible in an image; a graphics generator unit, responsive to the image processor, operational to generate from identified center points of the anatomical structures, a linear representation of an arrangement of the anatomical structures in the image, the linear representation comprising a set of three dimensional spatial coordinates including at least each of the identified center points of the anatomical structures; and a morphing processor unit, operatively coupled to the computer accessible memory, operational to access in the computer accessible memory a virtual model having a corresponding anatomical structure visible in the image, morphing processor unit further operational to morph parameters of the virtual model into a spatial arrangement that substantially mimics the corresponding anatomical structure visible in the image.

According to yet another aspect of the disclosure, a method for creating a visual simulation of a subject's condition, the method comprises: A) identifying a plurality of points defining the edges of at least one anatomical structure visible in an image of the subject; B) deriving, from the plurality of defined edges, a dead center point of a shape defined by the plurality of defined edges, the dead center point comprising a set of three dimensional spatial coordinates; C) manipulating three dimensional spatial coordinates of each of a plurality of points in a virtual model of the corresponding anatomical structure relative to the derived dead center point, wherein manipulating of the spatial coordinates of each of the plurality of points in the virtual model comprises any of translating, pivoting, rotating or proportionally scaling, spatial coordinates of each of a plurality of points in the virtual model relative to the derived dead center point; and D) repeating any of A), B) and/or C) for other anatomical structures visible in image of the subject.

According to yet another aspect of the disclosure, a method for creating a visual simulation of a subject's morphological condition, the method comprises: A) storing, in a computer accessible memory, a plurality of virtual models each of which represents a corresponding anatomical structure, the plurality of the virtual models having a predetermined spatial relationship representing a normal arrangement of corresponding anatomical structures; B) deriving, from at least one image of a subject, a subject morphology model comprising at least three dimensional spatial data identifying a spatial relationship of anatomical structures identified in the at least one image of the subject; and; C) morphing, with the subject morphology model, the predetermined spatial relationship of the virtual models into a spatial arrangement which substantially mimics the spatial relationship of the anatomical structures identified in the at least one image of the subject.

Disclosed are systems and methods for constructing a three dimensional simulation of the curvature of a boney structure, such as the spine, the model comprising a set of spatial coordinates derived from images of the bony structure captured in at least two different planes, and using that model, and medical data relating to the bony structure, e.g., scoliosis, to assist surgeons with determining the nature of a corrective procedure, predict postoperative changes in the curvature of the bony structure, the nature of the hardware necessary for use during the procedure and customizations of the hardware for the particular morphology of the patient will. The images of the bony structure may be captured by any type of medical imaging apparatus such as an X-ray apparatus, a magnetic resonance imaging (MRI) apparatus, or a computed tomography (CT) scanner.

Disclosed are systems and methods that provides an educational tool for both the surgeon and the patient. The system comprises a number of computational modules, including a curvature detection module, a morphing module, material analysis module, and a rendering module. The curvature detection module provides the primary input for morphing module, the material analysis module and rendering module, as explained hereafter.

The present disclosure features a method which includes obtaining or acquiring a first X-ray image of at least a portion of a spine in a first plane and obtaining or acquiring a second X-ray image of the at least a portion of a spine in a second plane. The method also includes superimposing simulated lines, on the first X-ray image and the second X-ray image, a line or curve that passes through vertebral bodies of at least a portion of a spine, calibrating the image data, and constructing a three-dimensional model of spatial coordinates describing the spine based on the lines or curves drawn on the first and second X-ray images. The method further includes determining parameters of a spinal device based on the three dimensional model and manufacturing or modifying the spinal device based on the three dimensional model.

According to embodiments of the present disclosure, the position of the spine and skull are quantified in three-dimensional space by performing image processing and analysis on at least sagittal and coronal X-rays of the spine. The resulting three dimensional model of the curvature of the spine may be used to morph a pre-existing model of a normal spine to simulate the morphology of the patient for pre-operative visualization and to further simulate the predictive outcomes visually of multiple degrees of corrective surgery.

In some aspects, the spinal device is a screw, a rod, a cervical plate, a spine implant, an interbody device, or an artificial disc.

In some aspects, the first plane is a coronal plane and the second plane is a sagittal plane.

In some aspects the method further includes obtaining a third X-ray image of at least a portion of the spine in an axial plane. In aspects, constructing the three-dimensional model includes constructing the three-dimensional model based on the lines or curves drawn on the first, second, and third X-ray images.

In some aspects, the method further includes identifying a line or curve on the first X-ray image and identifying a line or curve on the second X-ray image.

In some aspects, the lines are colored lines, and identifying the colored line includes quantifying the color of the colored lines and identifying differences in characteristics of the colored lines. In those aspects, the color of the colored lines includes at least one of Red, Green, or Blue, and the characteristics include at least one of intensity, hue, saturation, contrast, or brightness.

In some aspects, the method further includes calibrating the first X-ray image and the second X-ray image.

In some aspects, the method further includes obtaining coronal y-z coordinates or pixels of a central vertebral line with vertebral bodies and discs identified, and obtaining sagittal x-z coordinates or pixels.

In some aspects, the method further includes compensating for differences in magnification between the first X-ray image and the second X-ray image, and scaling the first and second X-ray images.

In some aspects, the method further includes combining the first and second X-ray images to construct the three-dimensional model.

In some aspects, the method further includes obtaining at least one four-dimensional model for a similar spine, analyzing the three-dimensional model based on at least one four-dimensional model to predict movement of the spine, and determining the parameters of the spinal device based on the predicted movement of the spine. In aspects, the similar spine is an abnormal spine, and the spine is a one-level degenerative disc case and the similar spine is a two-level degenerative disc case.

In some aspects, the method further includes acquiring medical data regarding a patient, analyzing the three-dimensional model in view of the medical data to predict movement of the spine over time, and determining the parameters of the spinal device based on the predicted movement of the spine.

In some aspects, the medical data includes at least one of diagnosis information, operative information, follow-up information, quality of life score, cardio information, diabetes information, or intra-operative information.

In some aspects, the quality of life score is selected from the group consisting of Visual Analog Scale (VAS), Oswestry Disability Index (ODI), Neck Disability Index, Rowland-Morris, Short Form Health Survey-12, Short Form Health Survey-36, Scoliosis Research Society-36 (SRS36), and Scoliosis Research Society-22 (SRS-22).

In some aspects, the method further includes generating instructions to construct the spinal device with a three-dimensional printer based on the parameters of the spinal device or instructions to modify the current configuration of an existing spinal device based on the three-dimensional model and any predicted changes to the spine model over time.

In aspects, the present disclosure features a method for performing spinal surgery. The method includes obtaining, over a predetermined period, a plurality of first images (e.g., X-ray or other images) of at least a portion of a first spine in a first plane and obtaining, over a predetermined period, a plurality of second images of the at least a portion of the first spine in a second plane. The method further includes drawing or superimposing a virtual line that passes through vertebral bodies of the at least a portion of the first spine in the plurality of first images and in the plurality of second images, acquiring medical data relating to the first spine, constructing a four-dimensional model based on the lines drawn on the pluralities of first and second images, analyzing the four-dimensional model in view of the medical data to predict movement of the first spine over time, obtaining medical data relating to the first spine, determining parameters of a spinal device based on the four-dimensional model and the obtained medical data, and deploying the spinal device in a second spine.

In aspects, the present disclosure features still another method of performing a surgical procedure. The method includes obtaining, over a predetermined period, a plurality of first images of a first plurality of skeletal bodies in a first plane, obtaining, over a predetermined period, a plurality of second images of the first plurality of skeletal bodies in a second plane, drawing a virtual line through the first plurality of bony structures or skeletal bodies in the pluralities of first and second images, constructing a four-dimensional model based on the lines drawn on the pluralities of first and second images, determining parameters of a medical device based on the four-dimensional model, forming a medical device based on the determined parameters; and applying the medical device to at least one skeletal body of a second plurality of skeletal bodies. In some aspects, the method includes the first and second pluralities of bony structures or skeletal bodies include bones of and/or associated with a hip, knee, or ankle.

In aspects, the present disclosure features a system for manufacturing a spinal device. The system includes a server, an X-ray apparatus, a computer, and a three-dimensional printer or milling machine. The server stores medical data. The X-ray apparatus captures a first X-ray image of a spine in a first plane and a second X-ray image of the spine in a second plane, and stores the first and second X-ray images in the server.

The computer includes a communications interface, one or more processors coupled to the communications interface, and a memory coupled to the one or more processor and having stored thereon instructions which, when executed by the one or more processors, causes the one or more processors to acquire via the communications interface the first X-ray image of the spine in the first plane and the second X-ray image of the spine in the second plane from the server, store the first and second X-ray images in the memory, acquire medical data relating to the spine from the server, store the medical data in memory, draw, on the first X-ray image and the second X-ray image, a curve through vertebral bodies of the spine, determine coordinates of the spine by detecting the curve on the first X-ray image and the second X-ray image, construct a three-dimensional model based on the curves on the first and second X-ray images, predict movement of the spine during a postoperative period based on the three-dimensional model and the medical data, which includes three-dimensional models of other spines, determine parameters of a spinal device based on the predicted movement of the spine, and transmit via the communications interface commands or instructions for forming a surgical device having the determined parameters.

The three-dimensional printer or milling machine acquires the commands or instructions and forms the surgical device based on the commands or instructions.

BRIEF DESCRIPTION OF THE DRAWINGS

Various aspects of the present disclosure are described hereinbelow with reference to the drawings, wherein:

FIGS. 19A and 19B are X-ray images in the sagittal and coronal planes of the Lumbar spine, respectively, annotated with a visually detectable scaling reference and the central points of vertebral bodies comprising the CVBL overlaid over the x-ray image in FIG. 19B;

FIG. 24A illustrates a three-dimensional model of the patient spine of FIG. 23A generated from CT scan data;

FIG. 24B illustrates a three-dimensional a simulation of the patient spine of FIG. 23A generated in accordance with the disclosure;

FIG. 26 is a screen shot of a user interface by which a surgeon/user may see enter various data in accordance with the disclosure.

DETAILED DESCRIPTION

Figure 1:
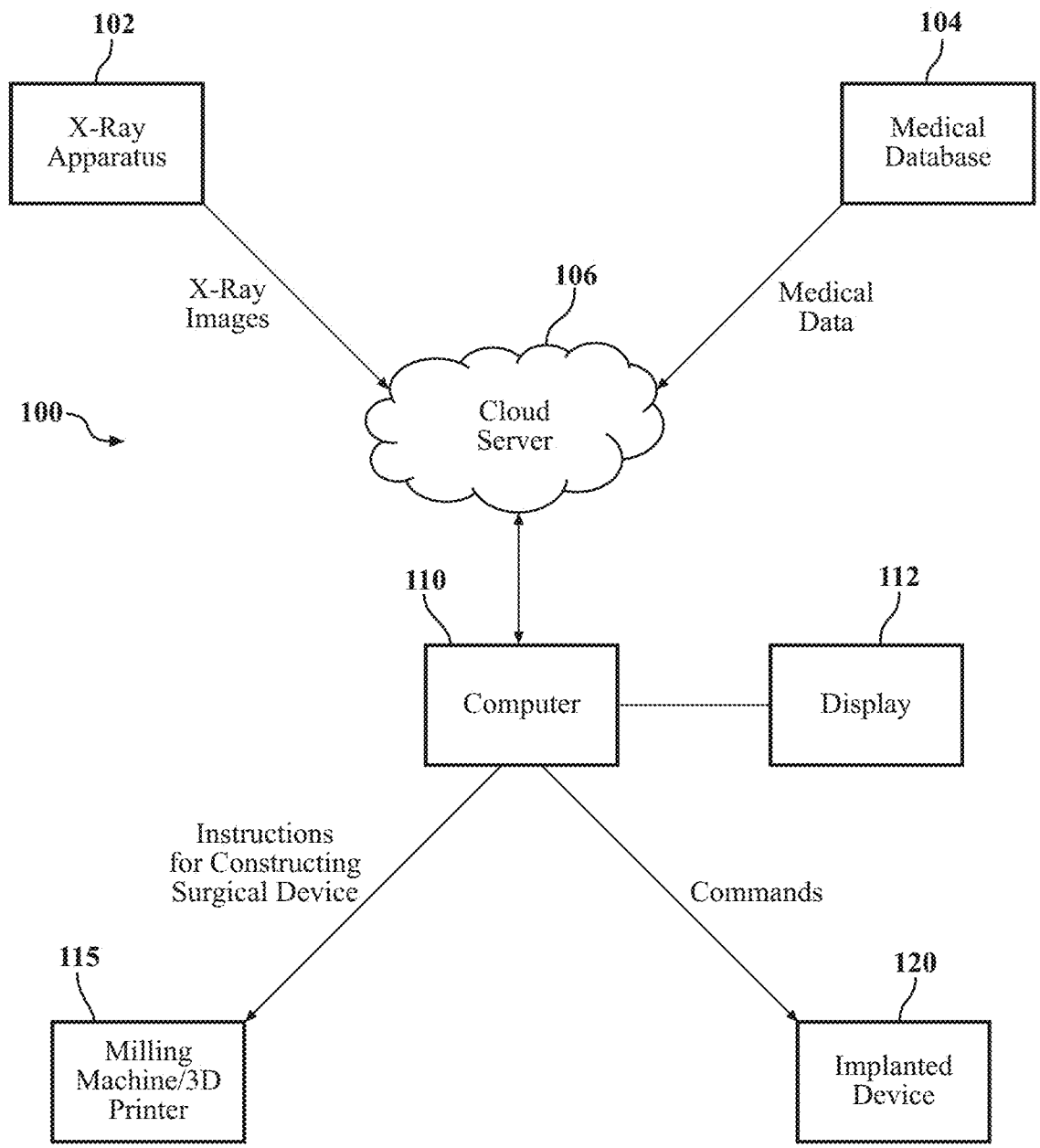
FIG. 1 is a block diagram illustrating a system architecture for performing spinal imaging, analysis, and surgery in accordance with some embodiments.

Embodiments of the present spine modeling systems and methods are now described in detail with reference to the drawings in which like reference numerals designate identical or corresponding elements in each of the several views. As used herein, the term "clinician" refers to a doctor, a nurse, or any other care provider and may include support personnel. Throughout this description, the phrase "in embodiments" and variations on this phrase generally is understood to mean that the particular feature, structure, system, or method being described includes at least one iteration of the disclosed technology. Such phrase should not be read or interpreted to mean that the particular feature, structure, system, or method described is either the best or the only way in which the embodiment can be implemented. Rather, such a phrase should be read to mean an example of a way in which the described technology could be implemented, but need not be the only way to do so.

As used herein, the term "sagittal plane" refers to a plane that divides the body into front and back halves and is parallel to an x-axis, the term "coronal plane" refers to a plane that divides the body into left and right (or posterior and anterior) portions and is parallel to a y-axis, the term "height" refers to a distance along a z-axis.

The goal of some spinal surgeries and the spinal devices that are used in those surgeries is to correct a spine so that it is in "sagittal balance." In short, sagittal balance means that the skull is positioned over or aligned with the pelvis. Many surgeons use software to guide them through the surgical procedure to ensure that "sagittal balance" is achieved. In some cases, while the surgeon may successfully place the spine in "sagittal balance," the spine may not be in "coronal balance" or, after the surgery, the spine may shift out of "coronal balance."

According to embodiments of the present disclosure, the position of the spine and skull are quantified in three-dimensional space by performing image processing and analysis on at least sagittal and coronal X-rays of the spine. The resulting three-dimensional model of the curvature of the spine may be compared to three-dimensional models of the curvature of other spines and analyzed in view of medical data related to the spine to determine an appropriate treatment plan to ensure both sagittal and coronal balance. The treatment plan may include constructing or modifying a surgical device and deploying it in, on, or near the spine based on the analysis of the three-dimensional model of the target spine. The resulting three-dimensional model of the curvature of the spine may also be used to morph a pre-existing model of a normal spine to simulate the morphology of the patient for pre-operative visualization and to further simulate the predictive outcomes visually of multiple degrees of corrective surgery.

FIG. 1 is a block diagram illustrating an exemplary system architecture for performing spinal imaging, analysis, and surgery in accordance with some embodiments. In some embodiments, an X-ray apparatus 102 provides X-ray images to a cloud server 106. The cloud server 106 may be secured in such a way that it complies with the privacy protection provisions of the Health Insurance Portability and Accountability Act of 1996 (HIPAA). In other embodiments, the X-ray apparatus 102 provides X-ray images to a computer or a server that may better protect patient information than cloud server 106. The X-ray apparatus 102 may be any X-ray apparatus that is configured to capture X-ray images of the human skeleton. The system architecture 100 may also include a medical database 104 that transmits and stores medical data in the cloud computer or server 106. The medical database 104 may reside in a doctor's office or in a hospital and may contain a variety of medical data that is useful in determining the method of performing spinal surgery and the parameters of the spinal device that is used to correct the misalignment of the spine. This medical data may include all medical conditions that are or may be relevant to the spine, including, for example, osteoporosis, adolescent idiopathic scoliosis, adult scoliosis, neuromuscular disease, and degenerative disc disease. In embodiments, the medical data may include one or more of the following: patient demographics, progress notes, vital signs, medical histories, human clinical data, diagnoses, medications, Cobb Angle measurements, adverse events, operative complications, implant complications, operative time, blood loss, immunization dates, allergies, X-ray images, such as coronal and sagittal X-ray images, and lab and test results.

Cloud computer server 106 may store the X-ray images and medical data in a way to allow for easy access by computer 110 that has access to the cloud computer or server 106. Computer 110 may display the X-ray images and the medical data to assist a clinician in planning for and performing a spinal surgery. Based on the X-ray images and the medical data, computer 110 may analyze X-ray images in the medical data to determine an appropriate method of performing a spinal surgery and/or the parameters of the medical device to ensure that proper alignment is achieved well after the spinal surgery is performed.

The computer 110 may then analyze the X-ray images and the medical data to determine instructions for constructing a surgical device or spinal device using milling machine or three-dimensional printer 115. In embodiments, printer 115 may be supplemented by or replaced by another manufacturing apparatus, such as a machine designed to bend spinal rods beyond their current configuration, such machine capable of responding to numeric data and instructions from communications interface 220. Alternatively or additionally, computer 110 may determine commands to send via a wireless communications link to a device that is implanted in, on, or near a spine. The commands may include a command to activate a motor to change a dimension of the implanted surgical device to change the position of at least a portion of the spine.

Figure 2:
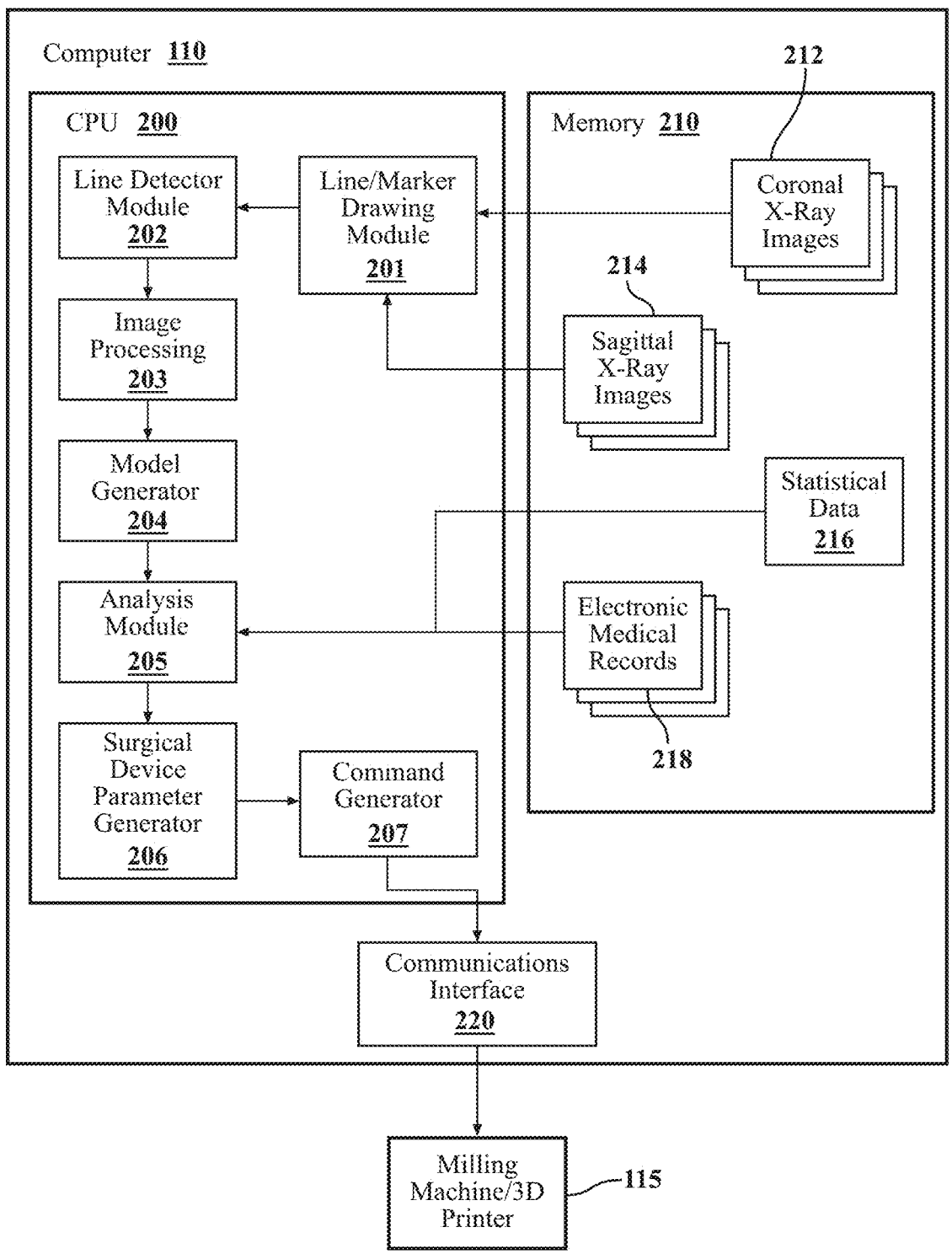
FIG. 2 is a block diagram illustrating a computer and surgical device manufacturing machine employed in the system architecture of FIG. 1.

FIG. 2 is a block diagram illustrating computer 110 coupled to milling machine/three-dimensional printer 115 employed in the system architecture 100 of FIG. 1. Computer 110 includes central processing unit 200 and memory 210. In some embodiments, a portion of the X-ray images stored in cloud server 106 are retrieved from the cloud server 106 by computer 110 and stored in memory 210. The X-ray images retrieved from cloud server 106 may include coronal X-ray images 212 and sagittal X-ray images 214 of one or more spines. Computer 110, under the control of the central processing unit 200, may also retrieve electronic medical records 218 from cloud server 106. Memory 210 may also store statistical data 216 that may be useful in analyzing coronal and sagittal X-ray images 212, 214, and electronic medical records 218.

Components of the system of the present disclosure can be embodied as circuitry, programmable circuitry configured to execute applications such as software, communication apparatus applications, or as a combined system of both circuitry and software configured to be executed on programmable circuitry. Embodiments may include a machine-readable medium storing a set of instructions which cause at least one processor to perform the described methods. Machine-readable medium is generally defined as any storage medium which can be accessed by a machine to retrieve content or data. Examples of machine readable media include but are not limited to magneto-optical discs, read only memory (ROM), random access memory (RAM), erasable programmable read only memories (EPROMs), electronically erasable programmable read only memories (EEPROMs), solid state communication apparatuses (SSDs) or any other machine-readable device which is suitable for storing instructions to be executed by a machine such as a computer.

In operation, the CPU 200 executes a line or marker drawing module 201 that retrieves the coronal X-ray images 212 and the sagittal X-ray images 214, and draws or superimposes a virtual line through the vertebral bodies of the spines shown in the coronal X-ray images 212 and the sagittal X-ray images 214. The line or marker drawing module 201 may also place markers on the spine to show different segments of the spine or to show inflection points on the spine. As is described in more detail below, the CPU 200 next executes a line detector module 202 that detects and determines the coordinates of the line drawn on each of the coronal X-ray images 212 and the sagittal X-ray images 214.

Next, the CPU 200 executes image processing 203 to scale or otherwise modify the coronal X-ray images 212 and the sagittal X-ray images 214 so that the lines or curves corresponding to the spine, and the coronal and sagittal X-ray images 212, 214 are scaled correctly with respect to each other so that they may be combined with each other into a three-dimensional or four-dimensional model of one or more spines.

The central processing unit 200 also executes a model generator 204. The model generator 204 takes the line or curve information and generates a three-dimensional model of the deformed spine. The central processing unit 210 then executes an analysis module 205 that analyzes one or more of statistical data 216, electronic medical records 218 retrieved from memory 210, and the three-dimensional or four-dimensional models generated by the model generator 204 to determine or predict postoperative changes in the curvature of the spine.

The central processing unit 200 also includes a surgical device parameter generator 206. The surgical device parameter generator 206 uses the determined or predicted postoperative changes in the spine to determine parameters of a surgical device, such as a spinal implant, that can counter the predicted postoperative changes in the spine to ensure proper alignment of the spine postoperatively. The central processing unit 200 may optionally include a command generator 207 for generating commands or instructions for controlling the milling machine or three-dimensional printer 115 to form or construct surgical device according to the parameters generated by the surgical device parameter generator 206. The computer 110 also includes a communications interface 220 that is in communication with the milling machine or three-dimensional printer 115 to provide commands or instructions to the milling machine or three-dimensional printer 115. In embodiments, three-dimensional printer may be supplemented by or replaced by another manufacturing apparatus, such as a machine designed to bend spinal rods beyond their current configuration, such machine capable of responding to numeric data and instructions from communications interface 220. Alternatively, such numeric data and instructions may be provided through a user interface associated with communications interface 220 in which the data may be presented to a user for manual manipulation of a spinal device.

Figure 3:
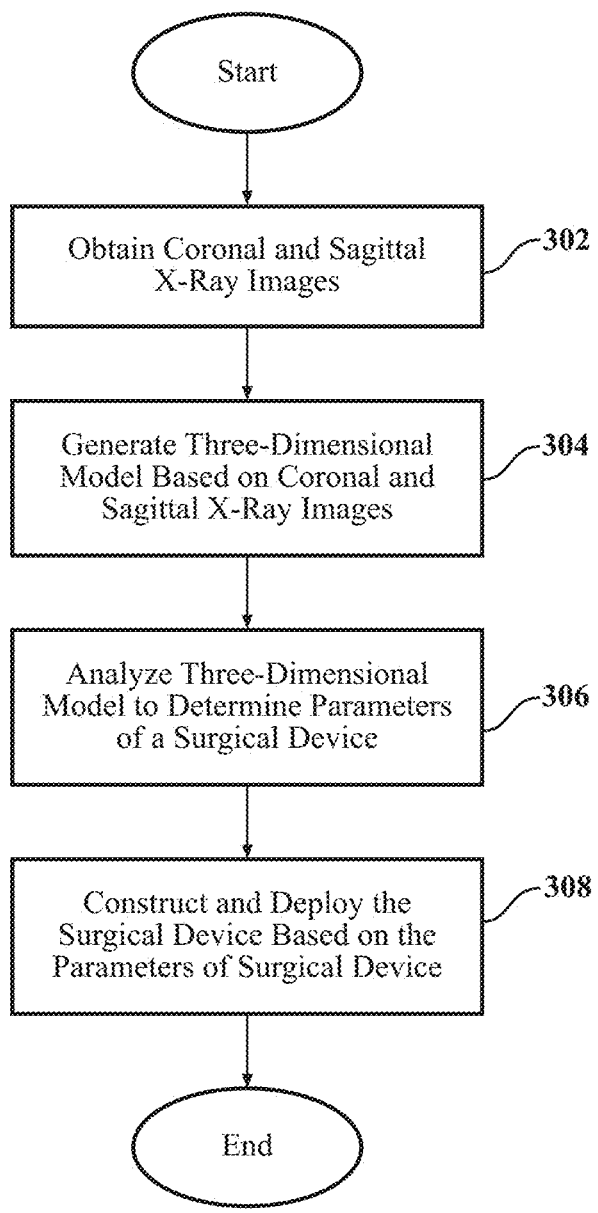
FIG. 3 is a flow diagram illustrating a process for performing a spinal surgery in accordance with some embodiments.

FIG. 3 is a flow diagram illustrating a process for performing spinal surgery in accordance with some embodiments. After starting, the coronal and sagittal X-ray images are obtained from a cloud computer or other similar database at block 302. The coronal and sagittal X-ray images may be X-ray images of a spine and may be obtained prior to the surgical procedure. The X-ray images may also include images that were obtained both before and after a previous surgical procedure, e.g., a procedure performed on the spine.

At block 304, a three-dimensional model is generated based on coronal and sagittal X-ray images. In embodiments, the resolution of the of the X-ray images is greater than the variation in size of the implants. For example, the resolution of the X-ray images may be 0.4 mm, while the implants may come in sizes with 1 mm variation. As described in more detail below, the coronal and sagittal X-ray images are analyzed to determine coordinates of the spine in three dimensional space. In other words, X-ray images are processed to generate three dimensions, e.g., length, width, and height in millimeters.

At block 306, the three-dimensional model is analyzed to determine parameters of a surgical device and/or steps for performing a spinal procedure. The analysis may include comparing the three dimensional model to three-dimensional models of similarly situated patients. For example, if the X-ray images of similarly situated patients show a change in position or curvature of portions of the spine in a direction away from normal alignment after a surgical procedure to align the spine, it may be determined that the parameters or dimensions of the surgical device need to be adjusted to account for this change in position or movement.

At block 308, the surgical device is constructed, and for later deployment, deployed at or near the spine based on the parameters of the surgical device determined based on an analysis of at least the three dimensional model of the spine of the target patient. For example, the surgical device may be formed using a milling machine by inserting an object in the milling machine and providing instructions to the milling machine to remove material from the object to form a surgical device according to the parameters or dimensions determined during the analysis of the three-dimensional model. Alternatively, numeric data and instructions may be provided to another manufacturing apparatus, such as a machine designed to bend spinal rods beyond their current configuration, such machine capable of responding to numeric data and instructions from communications interface 220. Such numeric data and instructions may also be provided through a user interface associated with communications interface 220 in which the data may be presented to a user for manual manipulation of a spinal device.

Figure 4:
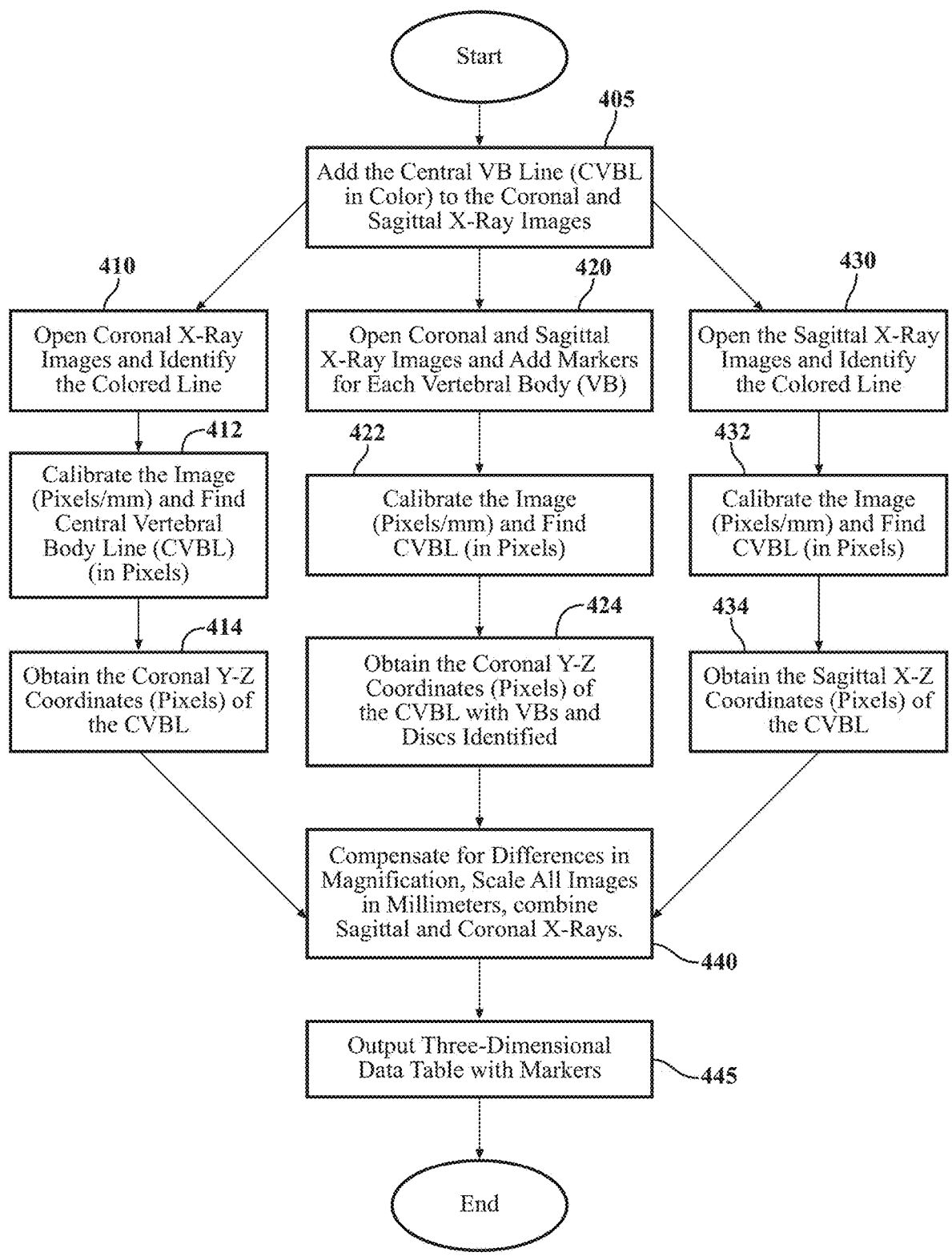
FIG. 4 is a flow diagram illustrating an example process for generating a model of a spine in the process of FIG. 3.

FIG. 4 is a flow diagram illustrating an exemplary process for generating a model of a spine in the process of FIG. 3. At block 405, image analysis software is utilized to identify and mark the center of each vertebral body recognized within the image and to construct a line or curve therefrom is drawn on or superimposed on over the vertebral bodies of the spine shown in each of the coronal and sagittal X-ray images. The curve or line, also referred to as a central vertebral body line, may be one color or a combination of colors. The color of the curve or line may be selected to optimize the detection of the curve or line superimposed on the coronal and sagittal X-ray images. For example, different colored segments of the line or curve may represent different of any of the cervical, thoracic, lumbar or sacral sections of the spinal column.

At block 410, the coronal X-ray images are opened and the colored lines or curves are identified or detected. This may be done by quantifying the color of the line or curve and search for differences in red, green, blue, intensity, hue, saturation, contrast, and/or brightness to identify or detect the central vertebral body line on the coronal X-ray image. For example, for a standard 36-inch X-ray, such a detection process may result in between 2500 and 3000 data points for the line or curve. The final number of data points is determined by the size of the image. In this way, the curvature of the spine is constructed and not the vertebral bodies themselves. Consequently, the three-dimensional models of the curvature of spines may be stored in memory using a small amount of memory resources. At step 412, the coronal X-ray images are calibrated and the central vertebral body line is found.

At block 420, the coronal and sagittal markers for each vertebral body are added to the images. At block 422, the images are calibrated and the central vertebral body line is found. Each x-ray has either an associated metadata file or scale bar on the image that enable image analysis software to determine a ratio of distance per image unit, e.g. typically expressed in centimeters per pixel. The image analysis software then identifies along each scan line of the x-ray, the coordinates of each point along the annotated line extending through the centers of vertebral bodies. Then, at block 424, the coronal and sagittal coordinates or pixels of the central vertebral body lines with the vertebral bodies and discs identified are obtained calculated utilizing the distance per pixel ratio, resulting in X-Z and Y-Z coordinate sets representing the lines in each of the sagittal and coronal planes, respectively.

At block 430, the sagittal X-ray images are opened and the colored lines or curves superimposed or drawn on the sagittal X-ray images are detected in the same manner as in block 410. At step 432, the coronal X-ray images are calibrated and the central vertebral body line is found. Then, in step 434, sagittal X-Z coordinates or pixels of the central vertebral body line are obtained. At block 440, the coronal Y-Z coordinates and the sagittal X-Z coordinates are compensated for differences in magnification are and scaled with a common unit. Then, the sagittal and coronal X-rays are combined along their respective Z axis values resulting in a series of spatial coordinates in Euclidean space which identify the three-dimensional curve of the subject's spine. At block 445, the three-dimensional model of the spine is stored in a data structure such as a table or array in which each of the columns represents a coordinate data point in one of the X, Y, Z axis and each row represents one of the points of the line representing the center of the vertebral bodies within the spine. More than one a three-dimensional data table may be generated to represent different three-dimensional models of the same spine relative to different reference axes.

Figure 5:
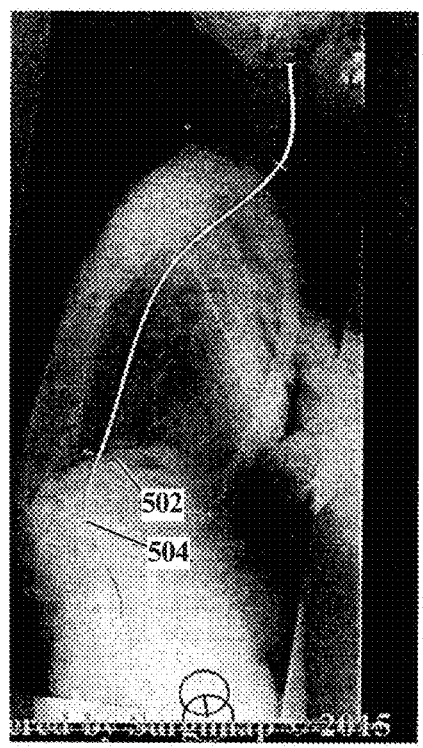
FIG. 5 is an X-ray image of a sagittal view of a preoperative spine illustrating the drawing of a virtual curve that passes through the vertebral bodies of the preoperative spine in accordance with some embodiments.

FIG. 5 is a user interface illustrating the drawing of a virtual curve through the vertebral bodies of a preoperative spine in a sagittal X-ray image in accordance with some embodiments. The central vertebral body curve or line 504 shows that the preoperative spine is not in proper alignment. Markers 502 indicate different portions of the spine.

Figure 6:
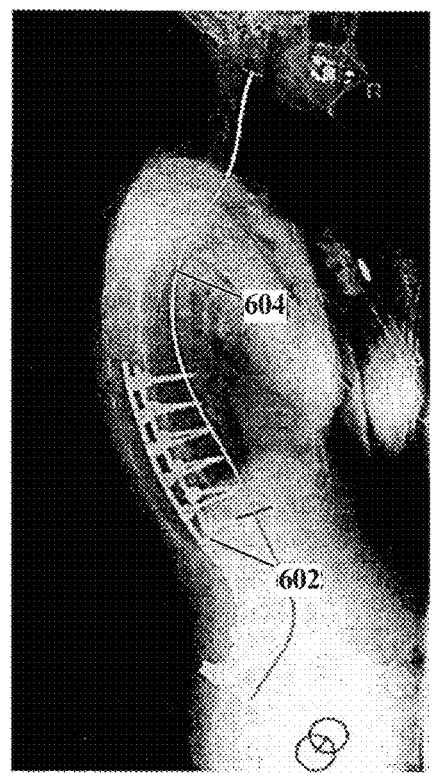
FIG. 6 is an X-ray image of a sagittal view of a postoperative spine illustrating the drawing of a virtual curve that passes through the vertebral bodies of the postoperative spine corresponding to the preoperative spine of FIG. 5 in accordance with some embodiments.

FIG. 6 is a user interface illustrating the drawing of a virtual curve through the vertebral bodies of a postoperative spine corresponding to the preoperative spine of FIG. 5 in accordance with some embodiments. The central vertebral body curve or line 604 shows that the postoperative spine in a sagittal X-ray image is in proper alignment because of the surgical device 602 implanted in the spine. The surgical device 602 is one of many examples of surgical devices that may be constructed and deployed in a human spine based on an analysis of the three-dimensional and four-dimensional models and medical data according to embodiments of the present disclosure.

Figure 7:
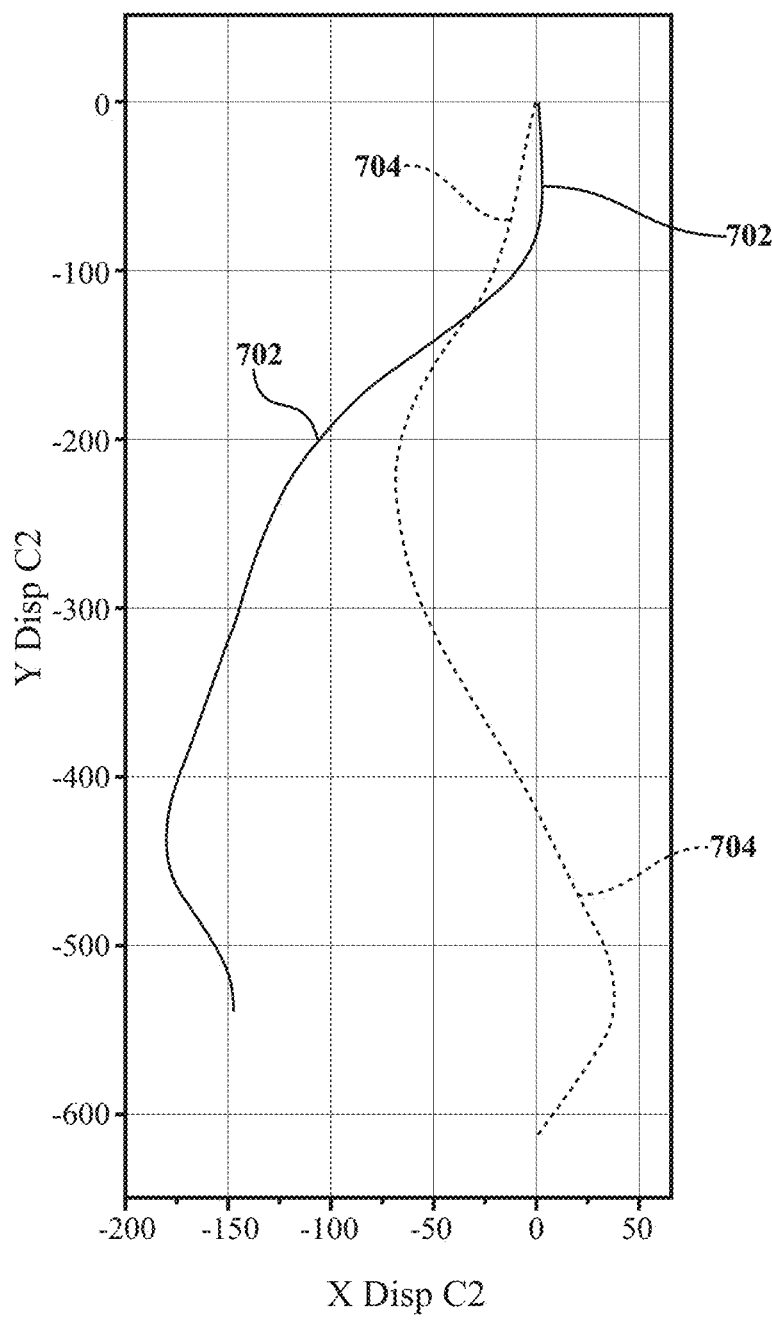
FIG. 7 is an example graph illustrating the curves extracted from the user interfaces of FIGS. 5 and 6.

FIG. 7 is an exemplary graph illustrating the curves extracted from the sagittal X-ray images of FIGS. 5 and 6. Curve 702 corresponds to the curve drawn on the sagittal X-ray image of FIG. 5 and curve 704 corresponds to the curve drawn on the sagittal X-ray image of FIG. 6. Curves 702 and 704 are obtained by quantifying the color of the curves 504 and 604 drawn on the sagittal X-ray images of FIGS. 5 and 6, and finding differences in red, green, blue, intensity, hue, saturation, contrast, and brightness to identify the central sacral vertical line at every pixel. This image processing may result in thousands of data points to form curves 702 and 704.

Figure 8A:
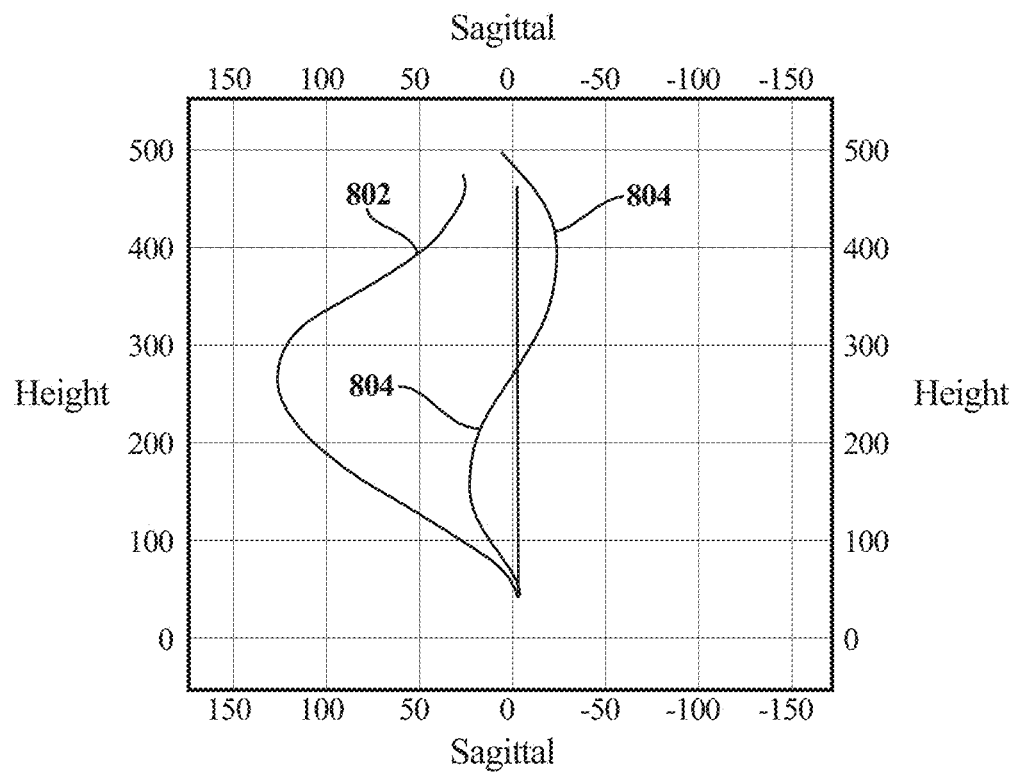
FIGS. 8A and 8B are diagrams illustrating the sagittal and coronal views, respectively, of preoperative and postoperative three-dimensional models of the curvature of a spine.
Figure 8B:
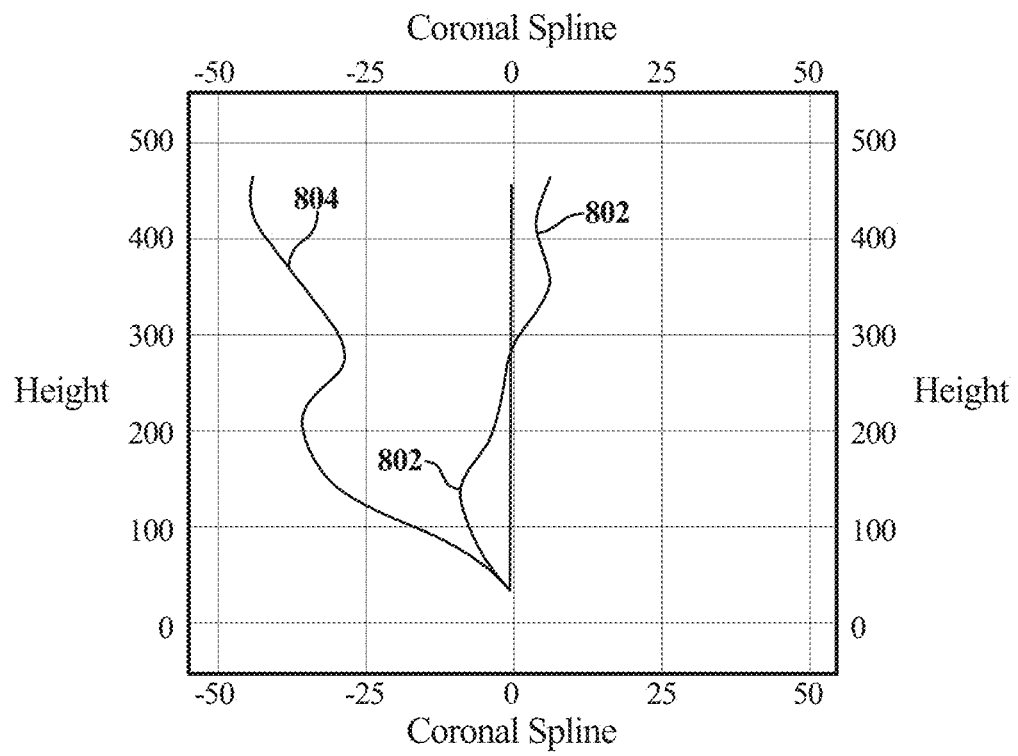

FIG. 8A is an exemplary graph illustrating a three-dimensional model rotated to the sagittal view. The three-dimensional model includes a preoperative curve 802 and a postoperative curve 804. The sagittal view of FIG. 8A shows that the surgeon corrected the spine to put it in proper alignment. However, as shown in FIG. 8B, in which the three-dimensional model is rotated to the coronal view, the spine is out of balance. The postoperative curve 804 shows that the patient is leaning the patient's right. In embodiments, this information is useful in performing future spinal surgeries on the patient whose spine is illustrated in FIGS. 8A and 8B, or on other patients who have not yet undergone surgery. For example, the surgical device may be designed to counter the spine's movement to the right as shown in FIG. 8B.

Figure 9:
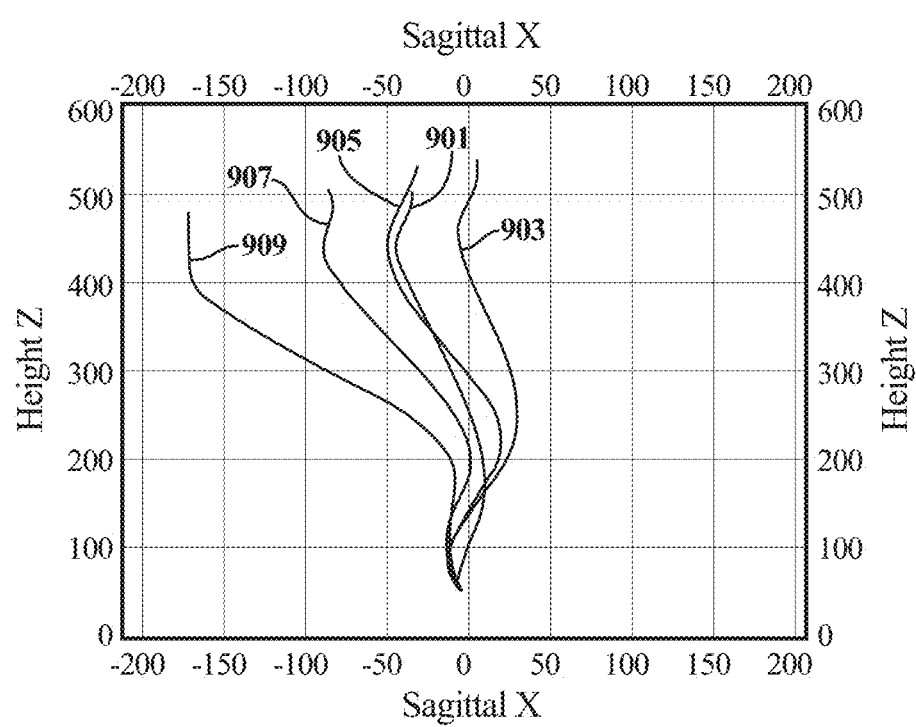
FIG. 9 is an example graph illustrating preoperative and postoperative three-dimensional models of the curvature of the spine for follow-up time periods in accordance with embodiments.
Figure 10:
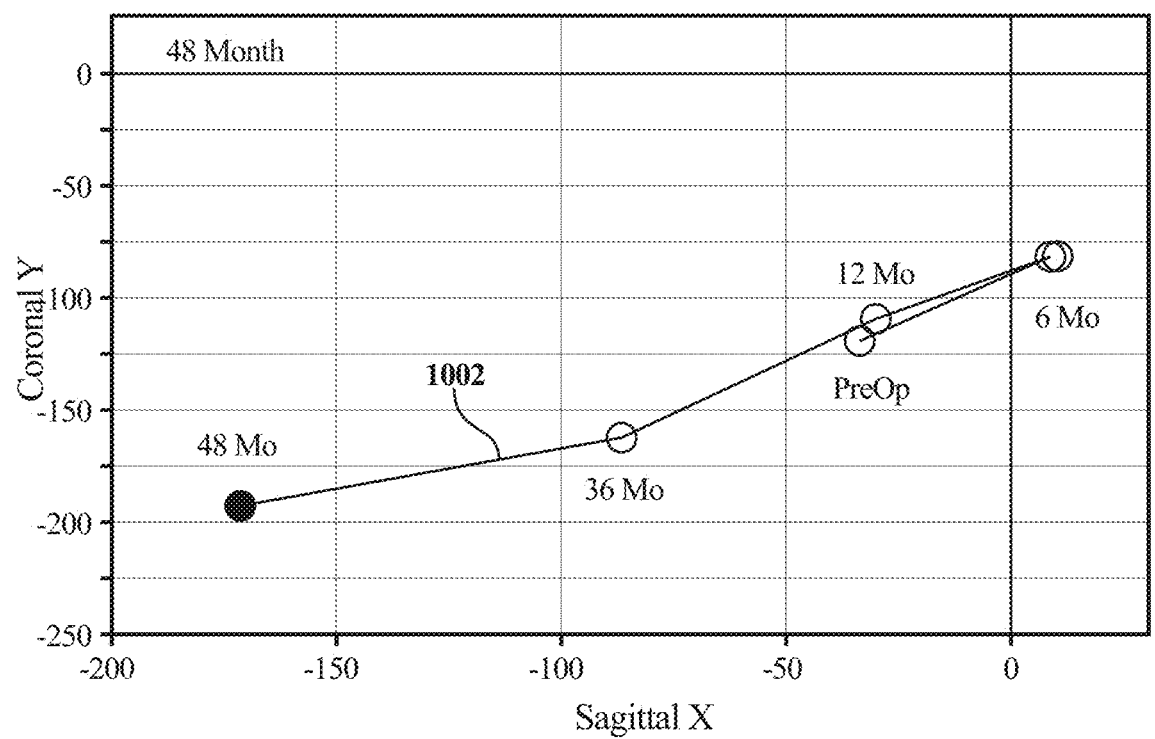
FIG. 10 is an example graph illustrating a four-dimensional model of the movement of a head from a preoperative state to a postoperative state.

FIG. 9 is an exemplary graph illustrating a three-dimensional model of a spine over a fourth dimension, e. g. time, from a preoperative state to a postoperative state at times 901, 903, 905, 907, 909, and FIG. 10 is an example graph illustrating a four-dimensional model of the movement of a head from a preoperative state to a postoperative state. As illustrated in FIGS. 9 and 10, the curvature of the spine, during a postoperative period, is changing from coronal and sagittal balance to an imbalanced state. In some embodiments, these models of the curvature of the spine over time may be used to predict the change in curvature of a spine of a similarly-situated patient who is being prepared for spinal-alignment surgery.

For example, as shown in FIGS. 9 and 10, the curvature of the spine that has undergone surgery is changing such that the position of the head is moving forward and to the right of a normal position of the head. If the patient of FIGS. 9 and 10 ("first patient") has similar preoperative spine positions and medical conditions as a patient who has not yet undergone a similar spinal surgery ("second patient"), the system of the present disclosure may predict that the second patient's spine will change positions in a way similar to the spine of the first patient. If there are any differences between the first and second patients, those differences may be used to adjust the predicted change in positions of the second patient's spine.

The predicted change in the positions of the second patient's spine may then be used to determine the parameters, e.g., dimensions, angles, or configurations, of the surgical device to be deployed in the second patient so as to counter the changes in positions of the second patient's spine in a case where the predicted changes in the positions of the second patient's spine results in at least one of coronal imbalance or sagittal imbalance. Once the coordinates in X-Y-Z dimensions are obtained, the determined parameters of the surgical device may be translated into instructions or commands for a milling machine or a three-dimensional printer to manufacture or form the surgical device.

Alternatively or additionally, the predicted change in the positions of the second patient's spine may be used to adjust the parameters, e.g., dimensions or configurations, of one or more adjustable surgical devices, e.g., intervertebral devices used to achieve a desired curvature of the spine, that already have been deployed in the second patient's spine. Examples of adjustable surgical devices are described in U.S. Pat. Nos. 9,585,762, 9,393,130, 9,408,638, 9,572,601, and 9,566,163, and in Pub. Nos. WO 2017/027873, US 2016/0166396, US 2016/0317187, and US 2016/0022323, the contents of each of which are hereby incorporated by reference in their entireties. Alternatively or additionally, the predicted change in the positions of the second patient's spine may be used to determine and employ appropriate surgical procedures for deploying a surgical device in the second patient's spine.

Figure 11:
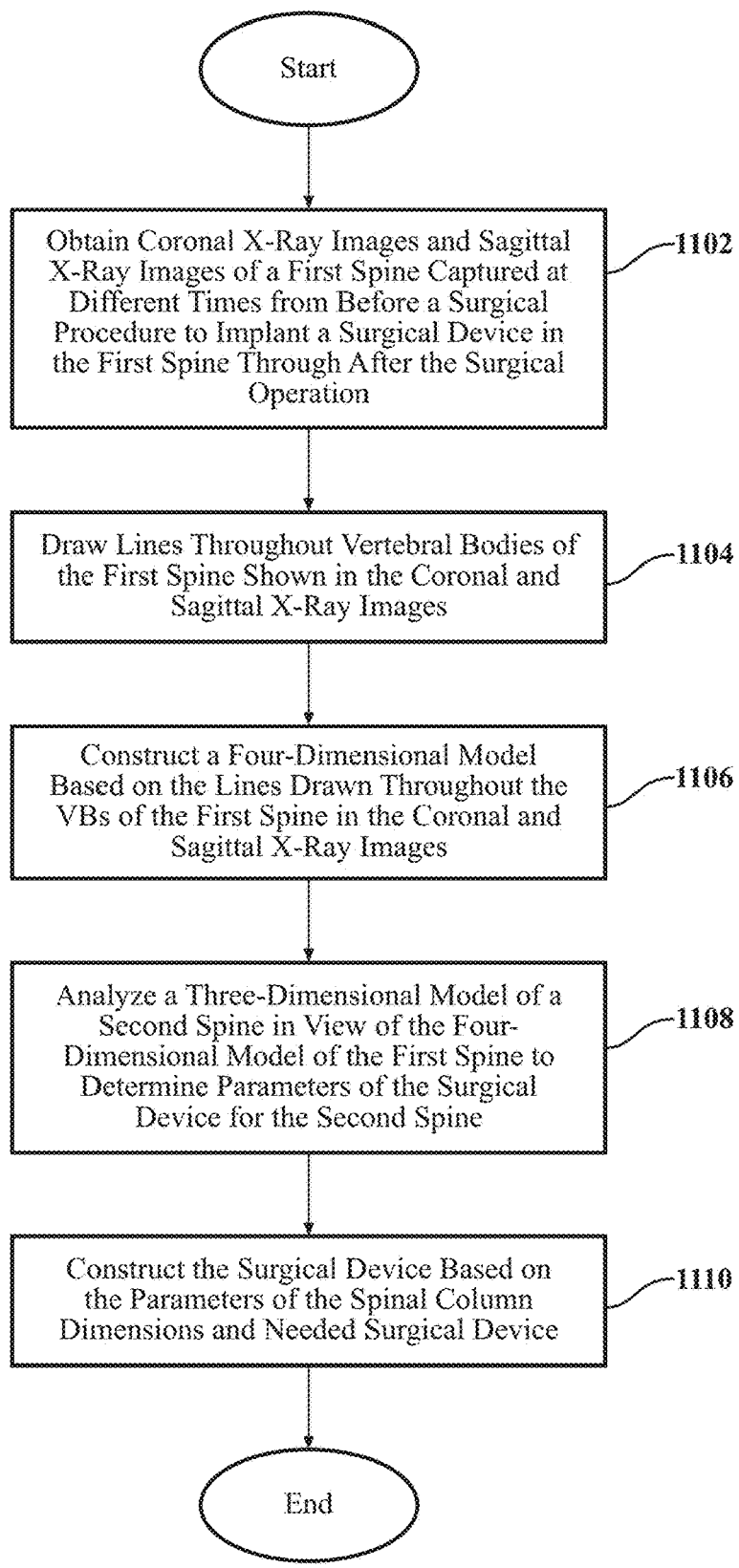
FIG. 11 is a flow diagram illustrating a process for performing spinal surgery using a four-dimensional model in accordance with some embodiments.

FIG. 11 is a flow diagram illustrating a process for performing spinal surgery using a four-dimensional model in accordance with some embodiments. At block 1102, a computer obtains coronal X-ray images and sagittal X-ray images of the first spine captured at different times. In some embodiments, the X-ray images are captured at different times during a preoperative period and during a postoperative period.

At block 1104, lines or curves are drawn through vertebral bodies of the first spine shown in the coronal and sagittal X-ray images. Specifically, image processing is applied to the coronal and sagittal X-ray images to recognize vertebral bodies and to locate a center point within the vertebral bodies through which the lines or curves may be drawn. At block 1106, a four-dimensional model is constructed based on the curves or lines drawn through the vertebral bodies of the first spine in the coronal and sagittal X-ray images. The lines or curves may be drawn by, for example, superimposing pixels of a particular color on the coronal and sagittal X-ray images. Alternatively, the lines or curves are drawn by replacing existing pixels of the coronal and sagittal X-ray images with replacement pixels of a predetermined color, e.g., cyan or magenta. This process of drawing a virtual line or curve may be done according to image processes known to those skilled in the art. Note, any color and virtual line are used as visual aids to assist in generating the CVBL. The module 2201 only needs several selected points on the image to interpolate the actual X, Y, and Z coordinates of the CVBL.

At block 1108, a three-dimensional model of a second spine is analyzed in view of the four-dimensional model of the first spine to determine parameters of the surgical device for the second spine. In some embodiments, the three-dimensional model of the second spine is also analyzed in view of medical data pertaining to both the first and second spines. For example, if the first and second spines are the same or similar in a preoperative state, and the medical data pertaining to both the first and second spines are similar, a prediction can be made that the first spine will behave similarly to the second spine during a postoperative period. Thus, the surgical device applied to the first spine may be adjusted to avoid any alignment issues that arise in the second spine during the postoperative period.

At block 1110, surgical device is constructed and deployed in the second spine based on the predictions made at block 1108 and based on parameters of the spinal column dimensions and needed surgical device.

Figure 12A:
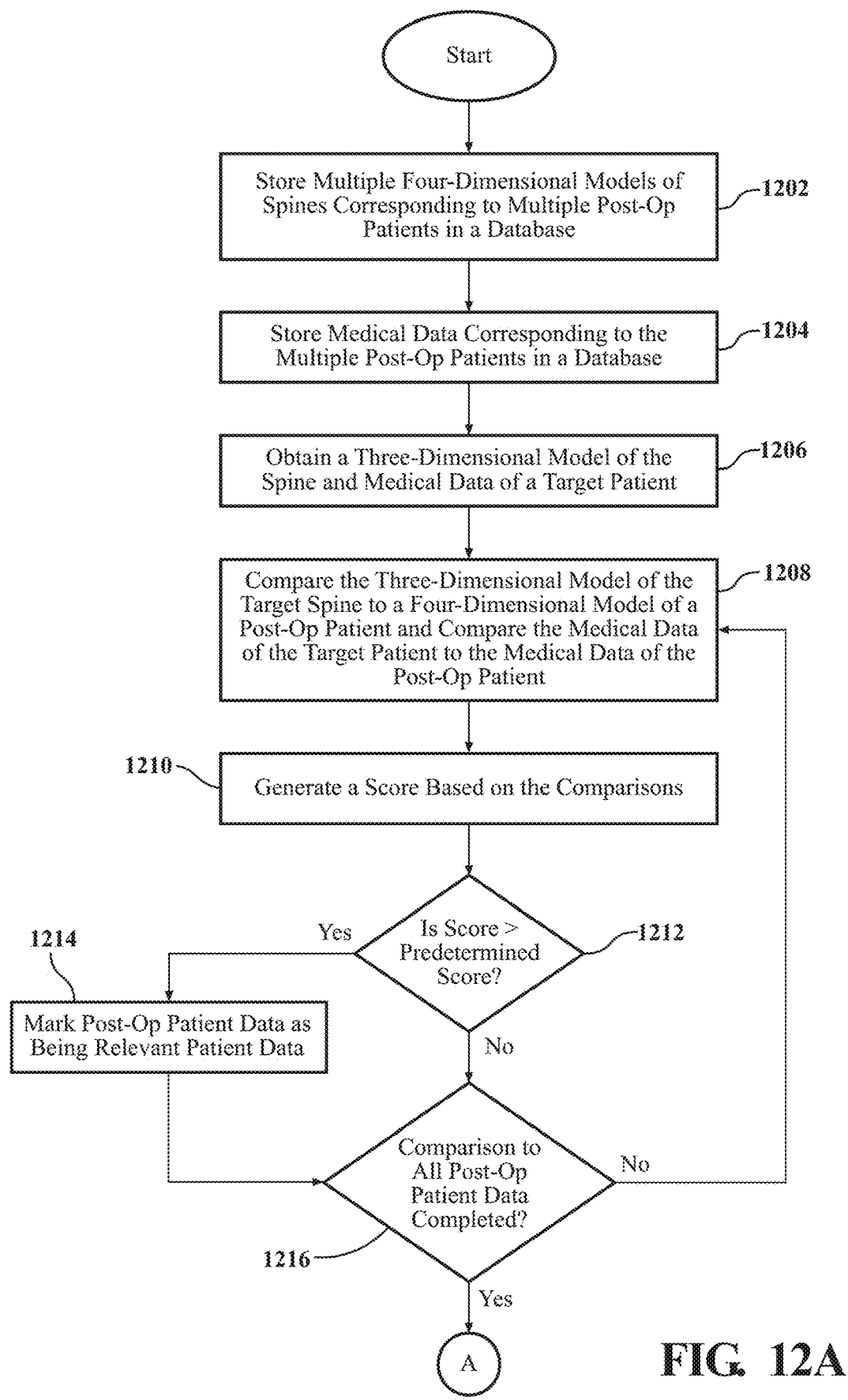
FIGS. 12A and 12B are flow diagrams illustrating a process for analyzing data from different patients and using that analysis to perform spinal surgery in accordance with some embodiments.
Figure 12B:
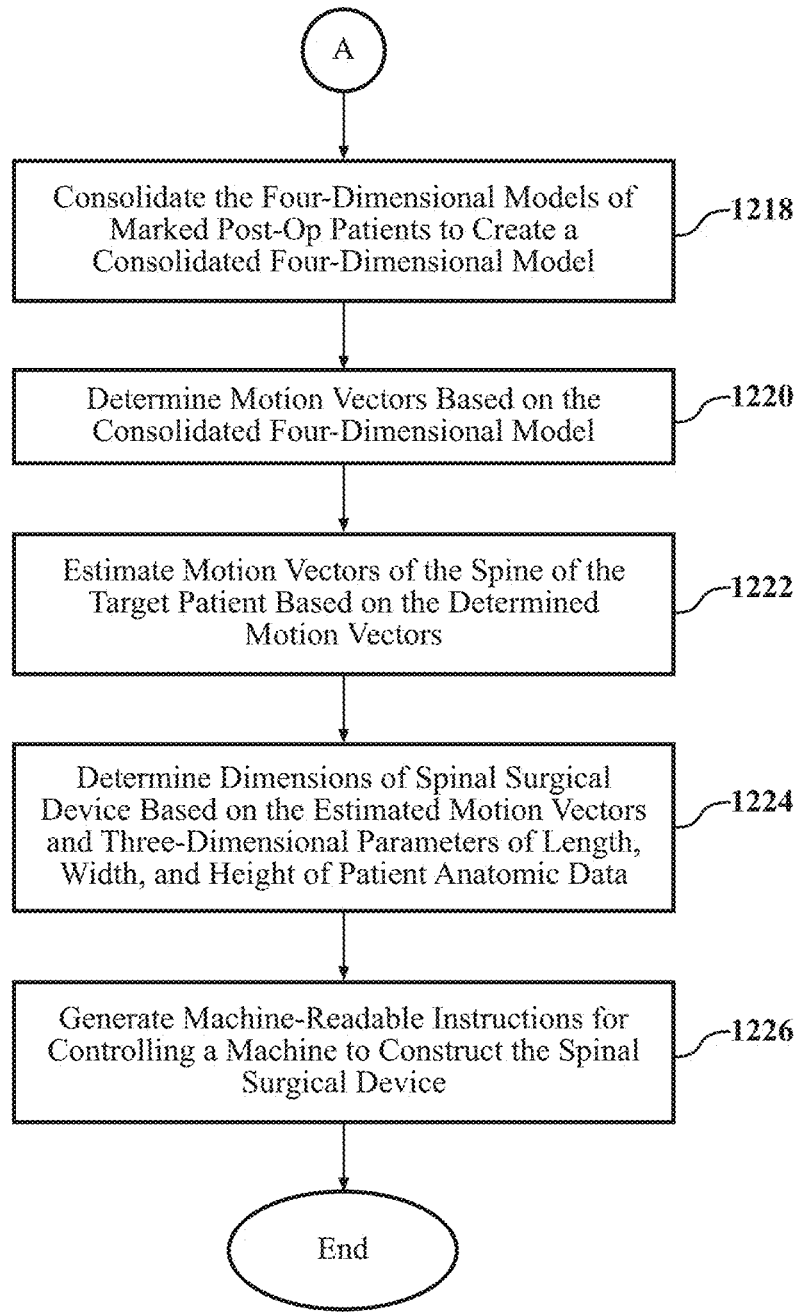

FIGS. 12A and 12B are flow diagrams illustrating a process for analyzing data from different patients and using that analysis to perform spinal surgery in accordance with some embodiments.

At block 1202, multiple four-dimensional models of spines corresponding to multiple postoperative patients are stored in a database. At block 1204, medical data corresponding to multiple postoperative patients is stored in a database as well. At block 1206, a three-dimensional model of the curvature of the spine and medical data of a target patient are obtained for analysis prior to a surgical procedure. At block 1208, the three-dimensional model of the target spine is compared to a four-dimensional model of the curvature of a spine of many postoperative patients and the medical data of the target patient is compared to the medical data of those post-operative patients. Then, at block 1210, a score may be generated based on the comparisons made between the models and between the medical data of the target patient and the postoperative patients.

For example, a higher score may be applied to a four-dimensional model that, in the preoperative state, most closely resembles the three-dimensional model of the target spine and the medical data of the target patient is closely related to the medical data of the postoperative patient. In embodiments, one score may be generated based on the comparison of the models and another score may be generated based on the comparison of the medical data.

At block 1212, the computer determines whether the score is greater than a predetermined score. If the score is greater than a predetermined score, the postoperative patient data is marked as being relevant patient data at block 1214. At block 1216, the computer determines whether comparisons have been completed for all postoperative patient data. If there is more post-op patient data, the process returns to step 1208 to compare models and medical data of the patients. If the comparisons have been completed, the four-dimensional models of marked postoperative patients are consolidated to create a consolidated four-dimensional model.

At block 1220, motion vectors are determined based on the consolidated four-dimensional model. At block 1222, motion vectors of the spine of the target patient are estimated based on the determined motion vectors. Then, at block 1224, dimensions of a spinal surgical device are determined based on the estimated motion vectors of the spine of the target patient and three-dimensional parameters of length, width, and height of patient anatomic data. At block 1226, machine-readable instructions for controlling a machine to construct the spinal surgical device are generated and are transmitted to the machine. In this manner, a surgical device may be constructed that accounts for estimated vectors to ensure that the target patient's spine maintains coronal and sagittal balance during the postoperative period. Alternatively, or in addition to, at block 1226, machine-readable instructions for controlling a machine to modify an existing spinal surgical device are generated and are transmitted to the machine, e.g. a machine designed to bend spinal rods beyond their current configuration.

In embodiments, the movement of the spine may be predicted using a model. In embodiments, the shape of a spine, whether it is normal or is deformed, can be defined by a mathematical equation. These equations can be modeled statistically using a spline or a nonlinear regression.

For example, a normal spine is made up of two, connected, logistic ogives, which are also known as sigmoidal or S-shaped curves. The ogives may take the following form:

$$Y=1/(1+e^{(\beta^*(\tau-X))})$$

The spline may be the easiest curve to fit and may provide useful information. The nonlinear regression provides more information, which, in certain applications, may be better.

Predictive analytics comes into play when the relevant medical data for a patient is known before the surgery. The relevant medical data may include the diagnosis, cobb angle, and/or Lenke classification. Then, a cohort of patients is found in a database that have the same or similar characteristic medical data.

For example, a new patient may be diagnosed with Adolescent Idiopathic Scoliosis (AIS) and a Lenke 1A curve. Before surgery, the relevant medical data for the new patient is known. In the database, there may be a number of old patients (e.g., 100 old patients) with AIS and Lenke 1A curves having the same or similar characteristic medical data. The medical data of the old patients in the database may include, among other medical data, the following: The surgical approach (Posterior versus Anterior versus Lateral); Levels fused, for example, T2 to T11, etc.; Type and size of hardware implanted (e.g., 5.5 mm rods, 6.5 mm screws; Titanium, Stainless steel); Operative time, blood loss, fluoroscope imaging time, ligaments resected, etc.; Follow-up information, complications, Health Related Quality of Life (HRQoL) scores.

Some or all of this medical data (which may be represented as variables) may be combined together using Boolean logic (e.g., AND, OR, NOT) as predictors to the new patient and factored in as probability functions. Then, an outcome metric is determined or chosen. For example, if global balance (which means head-over-pelvis) AND posterior surgical approach AND thoraco-lumbar junction was crossed AND titanium hardware (screws and rods) were used NOT (pelvic tilt (this measure was irrelevant) OR blood loss (did not matter)), the probability of success of the surgery for the new patient may be 92.4%. But if the transverse ligament is cut on the concave side (intraoperative data), the probability of success of the surgery for the new patient may drop to 73.5%. In embodiments, some or all of the relevant medical data may be used to predict movement of the new patient's spine after surgery, which, in turn, may be used to determine the probability of success of the surgery performed on the new patient's spine.

According to another aspect, the disclosed system and techniques utilize statistical analysis in conjunction with more accurate models of patients' spines to determine the parameters of spinal devices. The system and process for developing a three-dimensional model comprising a set of spatial coordinates which can be plotted in three dimensions and which characterizes the shape of the spine, not by angles but by spatial coordinates Euclidean space, has been described with reference to FIGS. 1 through 12 herein. As such, the nature of the spinal model allows it to be compared with other axes of reference and the variance there between quantified. In disclosed embodiments, the variance may be a numerical value used to indicate how widely spinal curvature fluctuates around the axis of the patient representing the head over pelvis (HOP).

Figure 13:
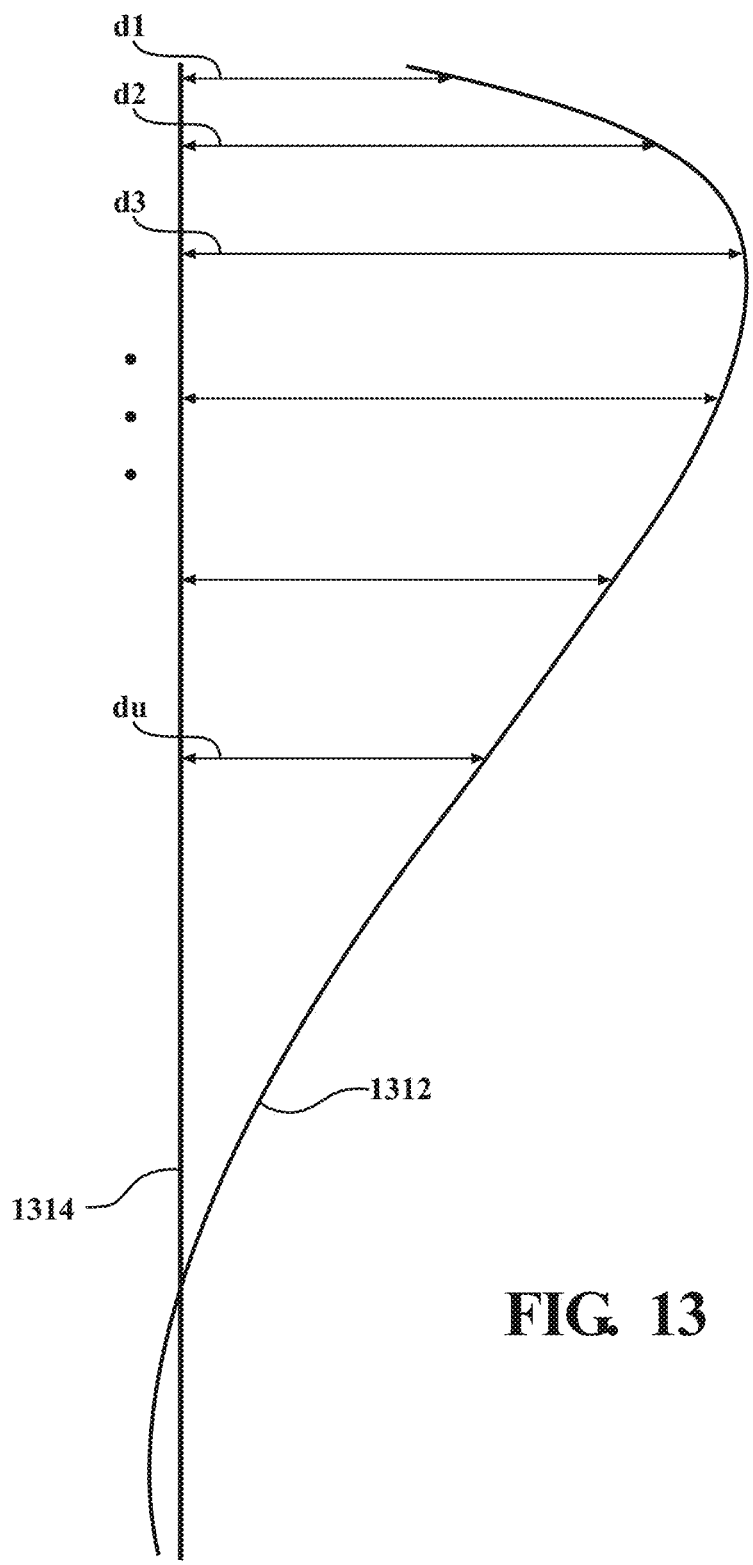
FIG. 13 is a conceptual illustration of a line representing the curvature of a model spine relative to the Z axis from one of the coronal or sagittal planes.

Referring to FIG. 13, a line 1312, representing the curved shape of a three-dimensional spinal model created in accordance with the techniques described herein, is shown in relation to a vertical line 1314 representing a reference axis, which in this example is the Z axis serving as an idealized head over pelvis line. Points comprising line 1312 each have a distance d1, d2, d3 . . . dn from line 1314, as illustrated. Utilizing a sum of squares calculation representing a summation of the squared value of these distance from the reference axis, a numerical variance value and standard deviation for each of the sagittal and coronal planes may be calculated and a composite total variance and standard deviation of the spine relative to the reference axis may be determined.

In the total variance of the compensated image data with an patient's HOP reference axis, idealized or otherwise, may be defined in Equation 1 below:

$$Total=VAR(X)+VAR(Y)$$

where VAR (X) represents the variance in the sagittal plane as defined in Equation 2 below:

$$\frac{\sum_{i=1}^{n}(HoP-X)^2}{n-1}$$

and where VAR (Y) represents the variance in coronal plane as defined in Equation 3 below:

$$\frac{\sum_{i=1}^{n}(HoP-Y)^2}{n-1}$$

The Sample Variance may then be represented as defined in Equation 4 below:

$$SS/(n-1)=\text{Sample Variance}$$

where SS represents the summation of the squares and n represents the number of data samples, e.g., the number of lines in the X-ray image. The Sample Variance may then be represented as defined in Equation 5 below:

$$\sqrt{SS/(n-1)}=\text{Sample SD}$$

Sample values for the Sum of Squares, Variance, and Standard Deviation, which are not meant to be limiting are set for below:
  Sum Squares
  Sagittal—2,259,488
  Coronal—11,114,040
  Total—13,372,147
  Variance
  Sagittal—3030
  Coronal—616
  Total—3656
  Standard Deviation
  Sagittal—55
  Coronal—25
  Total—60.5

Figure 14:
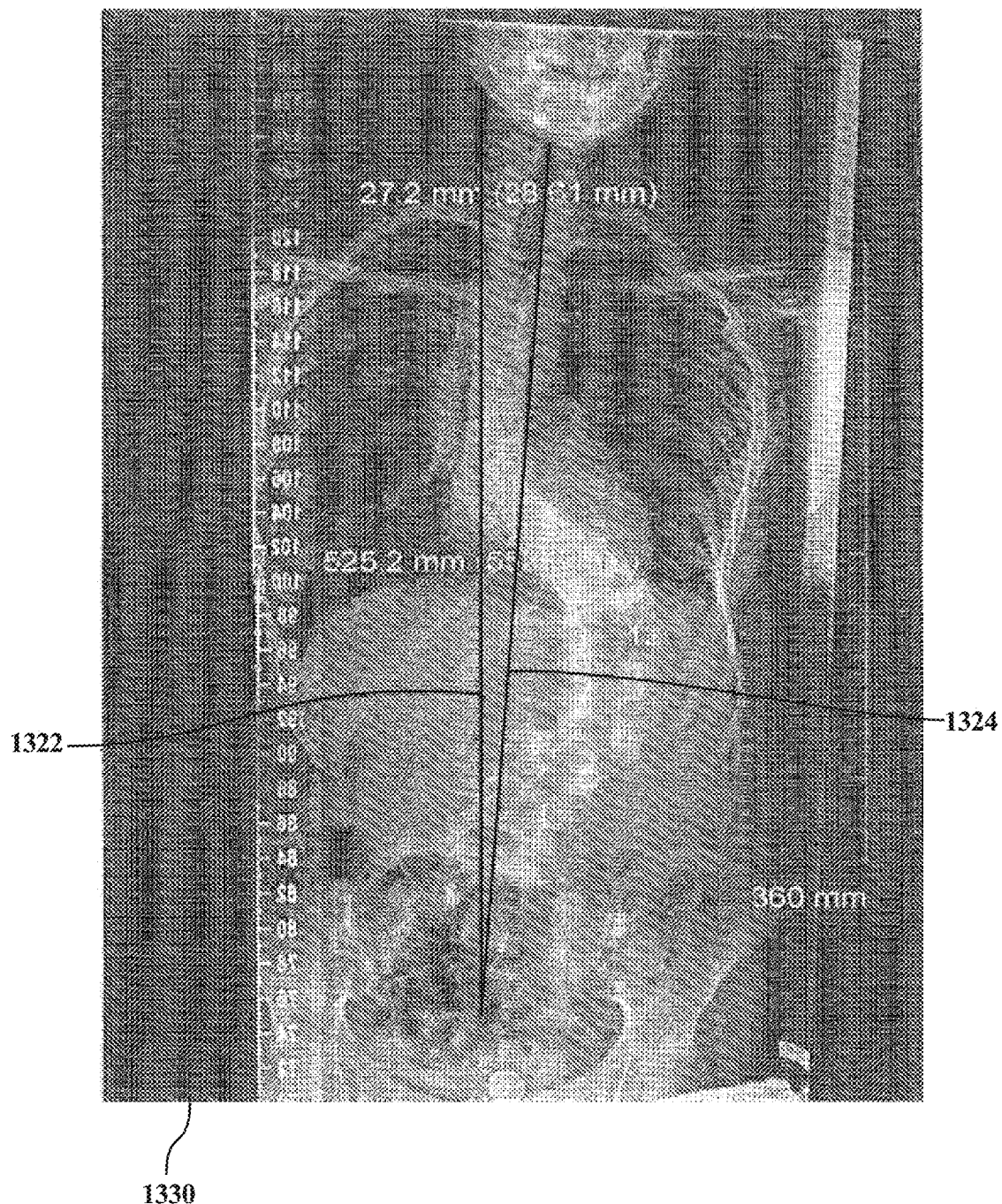
FIG. 14 is an X-ray image of a coronal view of a preoperative spine annotated with lines representing the Z axis and the patient HOP axis extending from the center of the pelvis to a vertebral body at the base of the skull.

If the head of the patient is angled, as illustrated in image 1330 of FIG. 14, the reference axis representing the HOP for a patient will not be line 1322, representing the Z-axis, but may be another axis such as line 1324, representing the actual HOP of the patient and which deviates at an angle from line 1332. In such instance, the variance may be further defined as in Equation 6 below:

$$\frac{\sum_{i=1}^{n}(\text{Mean}-X)^2}{n-1}$$

Utilizing the variance values as calculated and described herein enables practitioners to determine the extent to which a patient's spine deviates from a hypothesized reference axis and enables such variance value to be compared with other patient populaces to more easily determine if a procedure is either required or has been successful in comparison the prior patient populaces. Additionally, the variance value maybe used as a predictive indicator of the pressure and force to which a spinal device, a such as a rod, may subjected and may be further used to suggest parameters for modification or manufacturing of the spinal device, so that the faces to be used in spinal models having greater variance may need to be modified, e.g. over bending of rods in anticipation of torquing forces from the spine once implanted.

According to another aspect of the disclosure, systems and methods for rapid generation of simulations of a patient's spinal morphology enable pre-operative viewing of the patient's condition and to assist surgeons in determining the best corrective procedure and with any of the selection, augmentation or manufacture of spinal devices based on the patient specific simulated condition. The simulation is generated by morphing a generic spine model with a three-dimensional curve representation of the patient's spine derived from existing images of the patient's condition.

Figure 15:
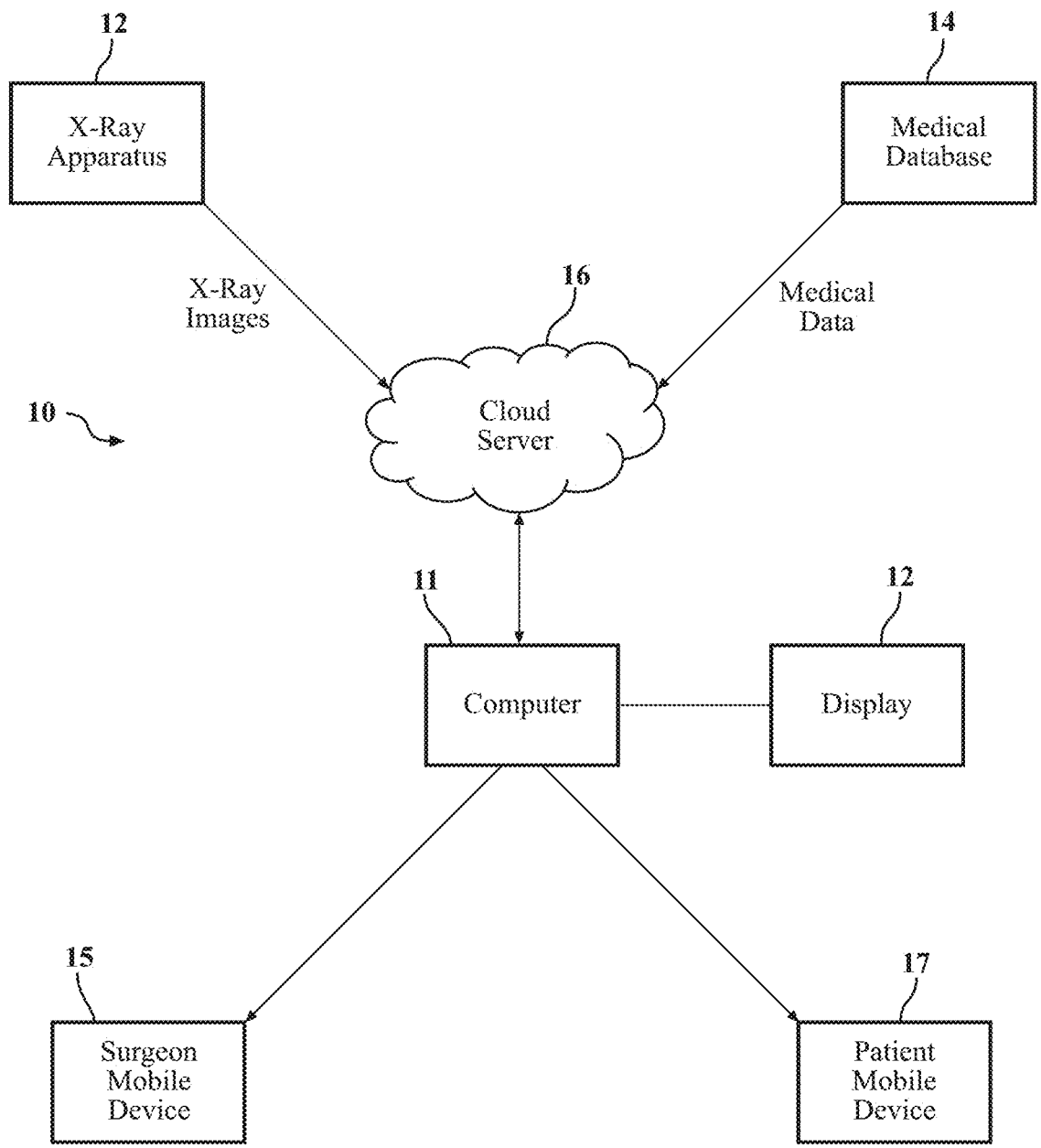
FIG. 15 is a block diagram illustrating a system architecture for performing spinal imaging, analysis, and simulation in accordance with the disclosure.

FIG. 15 is a block diagram illustrating an exemplary system architecture for rapid generation of simulations of a patient's spinal morphology. In embodiments, an X ray apparatus 12 provides X-ray images to a cloud server 16. The cloud server 16 may be secured in such a way that it complies with the privacy protection provisions of the Health Insurance Portability and Accountability Act of 1996 (HIPAA). In other embodiments, the X ray apparatus 12 provides X-ray images to a computer or a server that may better protect patient information than cloud server 16. The X ray apparatus 12 may be any X-ray apparatus that is configured to capture X ray images of the human skeleton. The system architecture 10 may also include a medical database 14 that transmits and stores medical data in the cloud computer or server 16. The medical database 14 may reside in a doctor's office or in a hospital and may contain a variety of medical data that is useful in determining the method of performing spinal surgery and the parameters of the spinal device that is used to correct the misalignment of the spine. This medical data may include all medical conditions that are or may be relevant to the spine, including, for example, osteoporosis, adolescent idiopathic scoliosis, adult scoliosis, neuromuscular disease, and degenerative disc disease. In embodiments, the medical data may include one or more of the following: patient demographics, progress notes, vital signs, medical histories, human clinical data, diagnoses, medications, Cobb Angle measurements, adverse events, operative complications, implant complications, operative time, blood loss, immunization dates, allergies, X-ray images, such as coronal and sagittal X-ray images, and lab and test results.

Cloud computer server 16 may store the X-ray images and medical data in a way to allow for easy access by computer 11 that has access to the cloud computer or server 16. Computer 11 using display 12 may display the X-ray images and the medical data to assist a clinician in planning for and performing a spinal surgery. The computer 11 may then analyze the X-ray images and the medical data to determine instructions for constructing a simulation of the spinal morphology of a patient's vertebral body for pre-operative visualization and to further simulate the predictive outcomes visually of multiple degrees of corrective surgery. The above described process is repeated for some or all of the other vertebral bodies in the spine, resulting in a three-dimensional simulation of the vertebral bodies in a patient spine, similar to that illustrated in FIG. 23B. During this process, the computer 11 may interact with a surgeon mobile device 15 or a patient mobile device 17 is illustrated.

Figure 16:
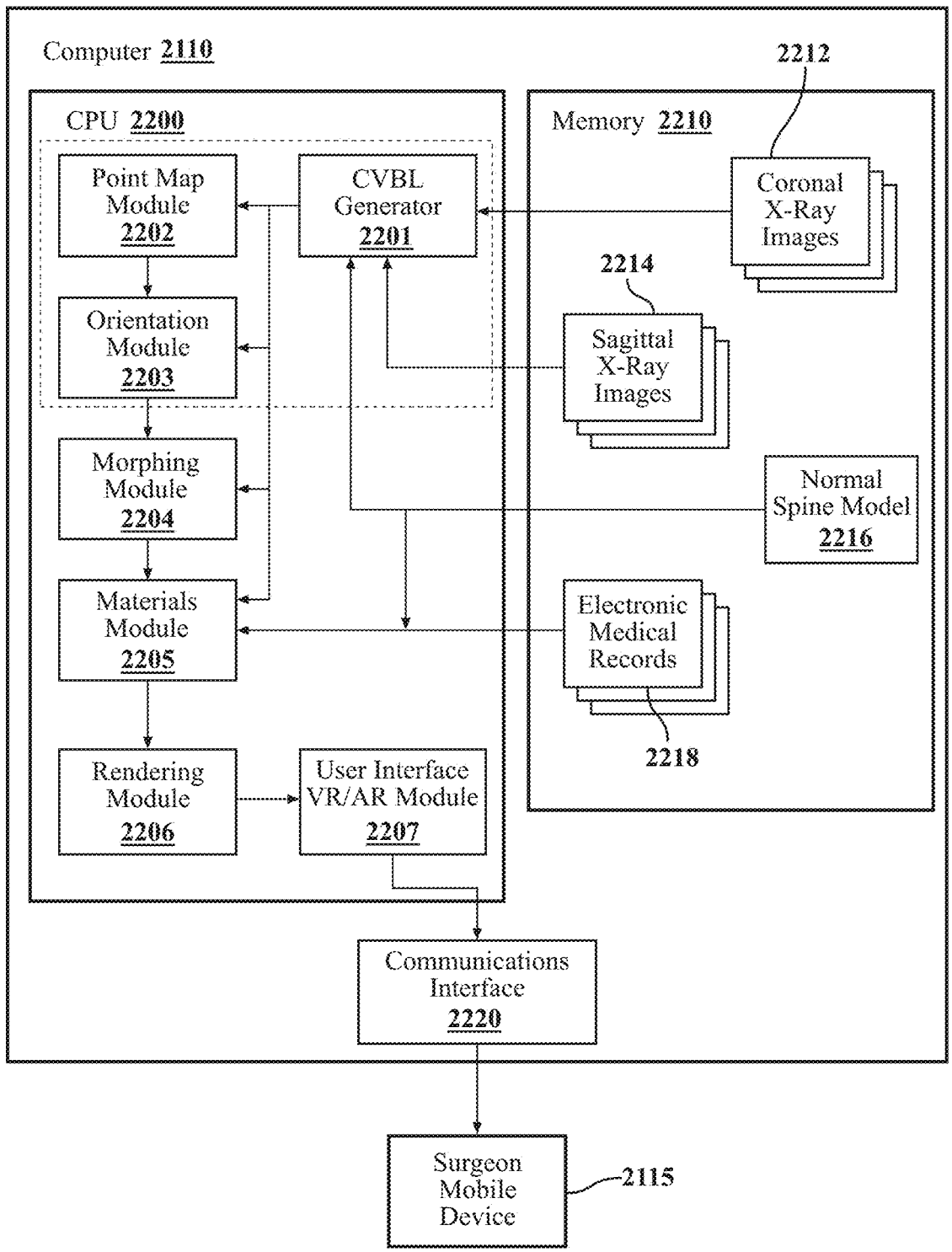
FIG. 16 is a block diagram illustrating a computer employed in the system architecture of FIG. 15 in accordance with the disclosure.

FIG. 16 is a block diagram illustrating computer 2110 and system architecture 10 of FIG. 15. Computer 110 includes central processing unit 2200 and memory 2210. In some embodiments, a portion of the X-ray images stored in cloud server 16 are retrieved from the cloud server 16 by computer 11 and stored in memory 2210. The X-ray images retrieved from cloud server 16 may include coronal X-ray images 2212 and sagittal X-ray images 2214 of one or more spines. Computer 11, under the control of the central processing unit 2200, may also retrieve one or more electronic medical records 2218 and/or spine models 2216 from cloud server 6. Memory 2210 may also store statistical data representing normal spine model 2216 that is used to generate a three-dimensional simulation of a patient's morphology. Note that module 2216 may store multiple different spine models that may be separately selectable based on different parameters such as any of gender, age, height range, weight range, specific pathologies, and/or risk factors such as smoking and/or alcohol use, etc. Such models may be in the form of a point cloud or may be in a format, such as CT scan data, from which a point cloud model may be derived.

Components of the system of the present disclosure can be embodied as circuitry, programmable circuitry modules configured to execute applications such as software, communication apparatus applications, or as a combined system of both circuitry and software configured to be executed on programmable circuitry. Embodiments may include a machine-readable medium storing a set of instructions which cause at least one processor to perform the described methods. Machine-readable medium is generally defined as any storage medium which can be accessed by a machine to retrieve content or data. Examples of machine readable media include but are not limited to magneto-optical discs, read only memory (ROM), random access memory (RAM), erasable programmable read only memories (EPROMs), electronically erasable programmable read only memories (EEPROMs), solid state communication apparatuses (SSDs) or any other machine-readable device which is suitable for storing instructions to be executed by a machine such as a computer. According to embodiments of the present disclosure, the CPU 2200 executes a number of computational modules, each of which is programmed to perform specific algorithmic functions, including a curvature detection module 2215, a morphing module 2204, material analysis module 2206, a rendering module 2206, and a User Interface module 2207. The curvature detection module 2215 further comprises a CVBL generator 2201, point map module 2202 and orientation module 203. Curvature detection module 2215 provides the primary input data for morphing module 2204 and material analysis module 2205. The morphing module 2204 morphs the three-dimensional simulated patient spine model into a preoperative condition, as explained herein yielding a three-dimensional simulated patient spine model, as illustrated in FIG. 23B. Material module 2205 enables altering the three-dimensional simulation by a predetermined amount or to the percent of correction from the surgeon input to enable preoperative visualization and/or prediction of the amount of correction required for a particular patient's spinal morphology. Rendering module 2206 visually creates an a virtual image to show the surgeon and/or patient the appearance of their spine, as simulated. The processes executed by CPU 2200 are described with reference to the flow diagrams of FIG. 17 and FIG. 18 below and as described elsewhere herein.

Figure 17:
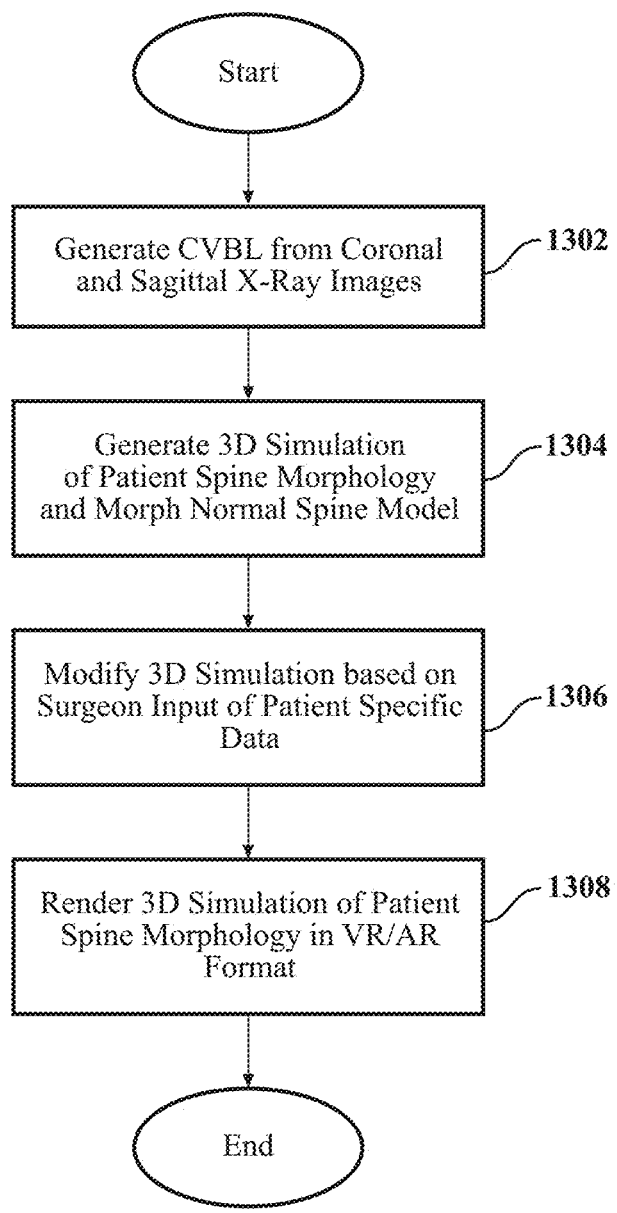
FIG. 17 is a flow diagram illustrating a process for generating a simulation of a patient's spinal morphology in accordance with the disclosure.
Figure 19C:
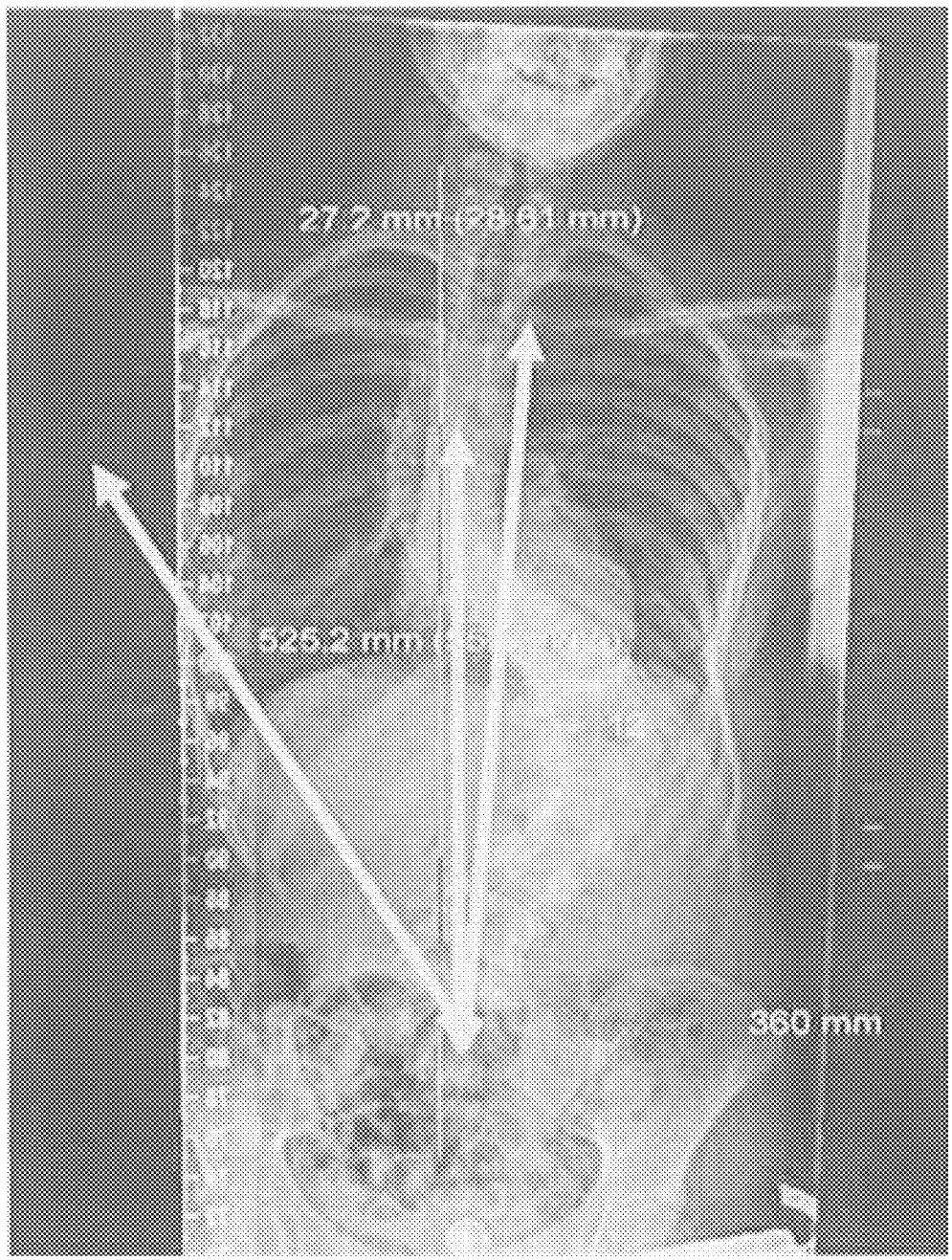
FIG. 19C is an X-ray image of a coronal view of a preoperative spine annotated with lines representing the Z axis and the patient HOP in accordance with the disclosure.

FIG. 17 is a flow diagram illustrating a process for performing spinal surgery in accordance with some embodiments. After the coronal and sagittal X-ray images are obtained from a cloud computer or other similar database, the CVBL generator 2201 processes the sagittal and coronal X-ray data, calibrates the image data to establish a common frame of reference, and then creates a Central Vertebral Body Line (CVBL), as illustrated at block 1302. Through either receipt of manually selected data received through user interface module 2207 or an automatic image detection algorithm executing within CVB of generator 2201, a series of points identifying the center of the vertebral bodies in a sagittal plane image and a coronal plane image are identified and stored by the CVBL generator 2201 which then calculates curvature and generates a spline representing the central vertebral body line in three dimensions. FIGS. 19A and 19B are X-ray images in the sagittal and coronal planes of the lumbar spine, respectively, annotated with a visually detectable scaling reference. In the coronal plane X-ray image 1900 of FIG. 19B the vertebral body central points 1902, 1904, 1906, 1908, and 1910 along spline 1920 are overlaid on the virtual x-ray image and illustrate a portion of the data utilized to generate a central vertebral line for the subject. Any image files or data format may be utilized, including DICOM images, by the CVBL generator 2201. The coronal and sagittal X-ray images may be X-ray images of a spine and may be obtained prior to the surgical procedure. The X-ray images may also include images that were obtained both before and after a previous surgical procedure, e.g., a procedure performed on the spine.

The three-dimensional simulation starts with either the creation or retrieval of a virtual model of each vertebral body in a set of vertebral body models and results in rendered vertebral bodies, as illustrated at block 1304. The curvature detection module 2215 and morphing module 2204 generate a three-dimensional simulation of a patient's spine morphology by morphing a normal spine model with a Central Vertebral Body Line representing an individual patient's spinal morphology to generate the three-dimensional simulation, as illustrated at block 1306, and as described herein. Next, the materials module 2205 enables the surgeon to input patient specific data which can be used to modify the three-dimensional simulation based on surgeon input of patient specific, as illustrated at block 1308. Rendering module 2206 and User Interface 2207 enable the three-dimensional simulation of the patient spine morphology, with or without further input from the surgeon, to be rendered in normal or Virtual-Reality/Augmented Reality (VR/AR) format, as illustrated at block 1308.

The disclosed system and techniques enable the morphing or alteration of a normal generic spine model into a three-dimensional simulation of the actual patient's deformity is derived from two-dimensional image data of the patient.

Disclosed are a number of different techniques for accomplishing these results. The process starts with a model of the spine, including each of the vertebral bodies of interest. In one embodiment, each vertebral body model is in the form of a point cloud representation of the vertebral body, the point cloud comprising as a series of points in three-dimensional space. Point clouds can be generated from any of a number of sources. The described processes may be used with vertebral body models comprising point clouds that are either commercially available models, or generated from a patient's own CT scan data, X-ray data, or other image data. For example, a three-dimensional scanner can generate the point cloud model from a patient's own X-ray images. A patient's own CT scan data can be used to derive point cloud model(s), even though the CT scan data includes more data than necessary for a point cloud model. The relevant amount of data to generate a point cloud model may be identified and extracted from the CT scan data either manually or with an automated program. Effectively the reason for generating a simulation even though a full set of CT scan data is available is that, with the simulation, not only does the practitioner have a simulation of the current state of the patient's spinal morphology, but is able to selectively morph the simulation into possible post-operative configurations based on user defined percentages of correction, i.e. 10%, 15%, etc. using the system and techniques as disclosed herein.

Figure 18:
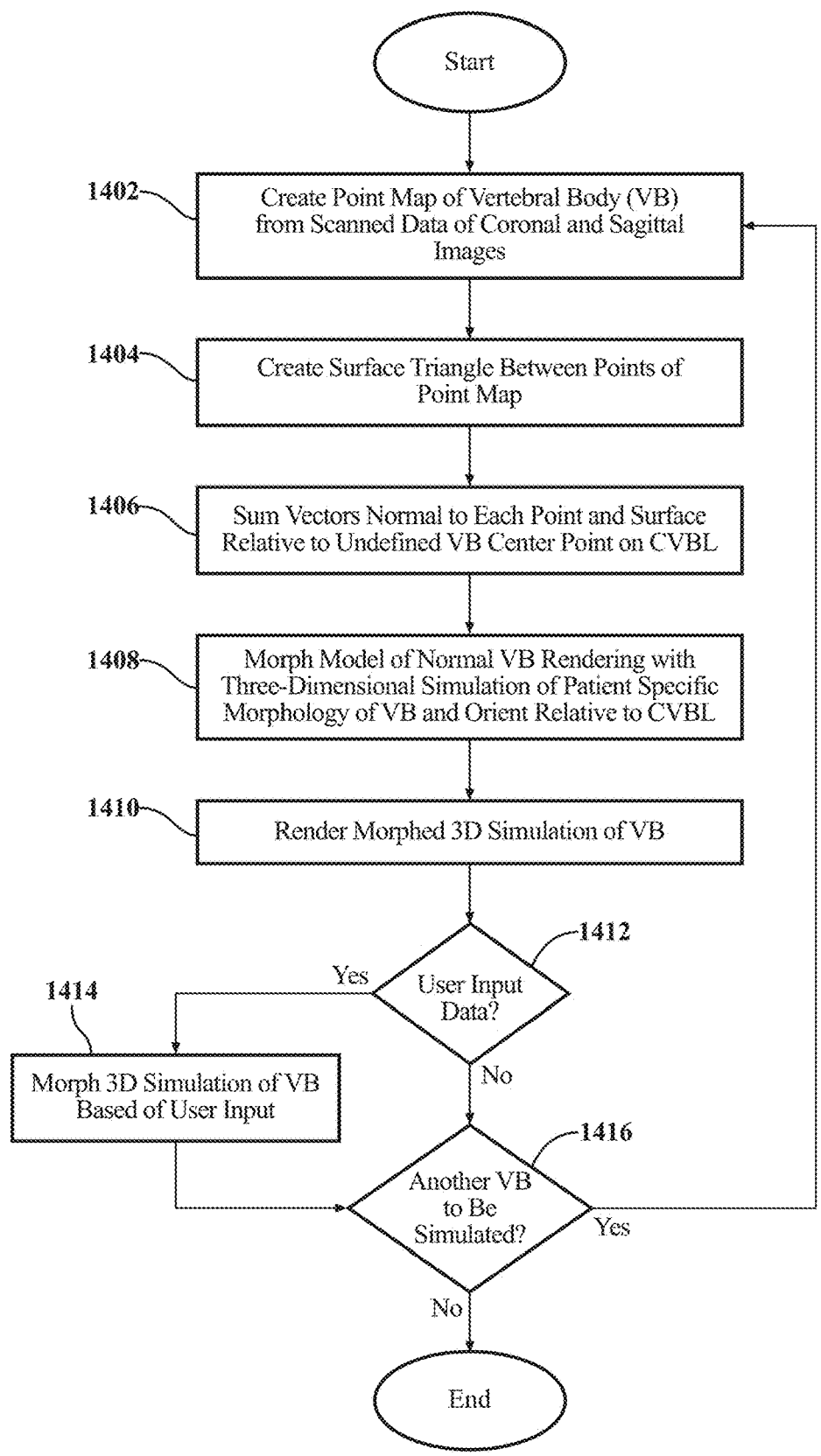
FIG. 18 is a flow diagram illustrating a sub-process of the process of FIG. 17 for generating a simulation of a patient's spinal morphology in accordance with the disclosure.
Figure 20A:
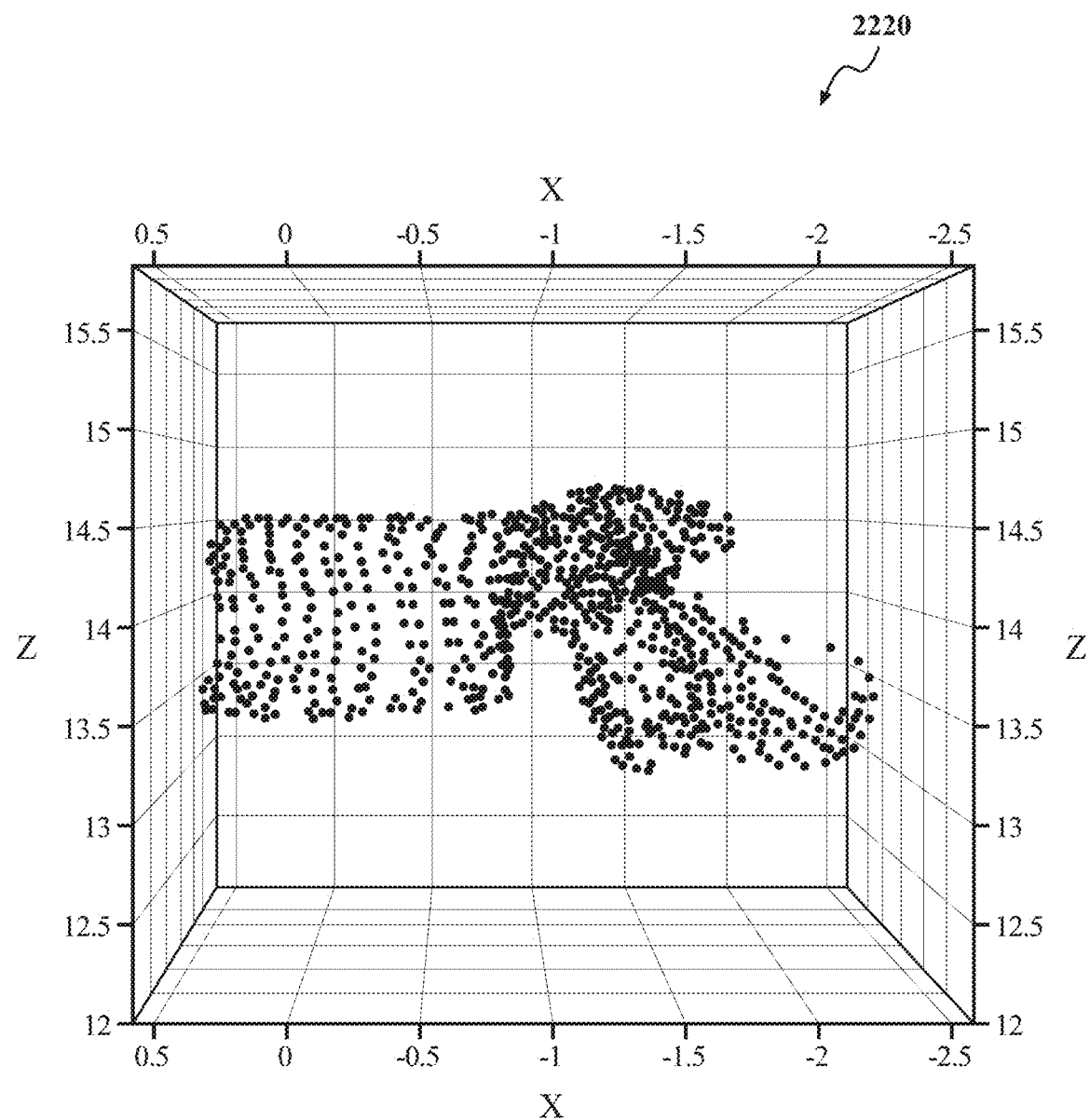
FIGS. 20A-B are three dimensional point maps representing a simulated vertebral body in accordance with the disclosure.
Figure 20B:
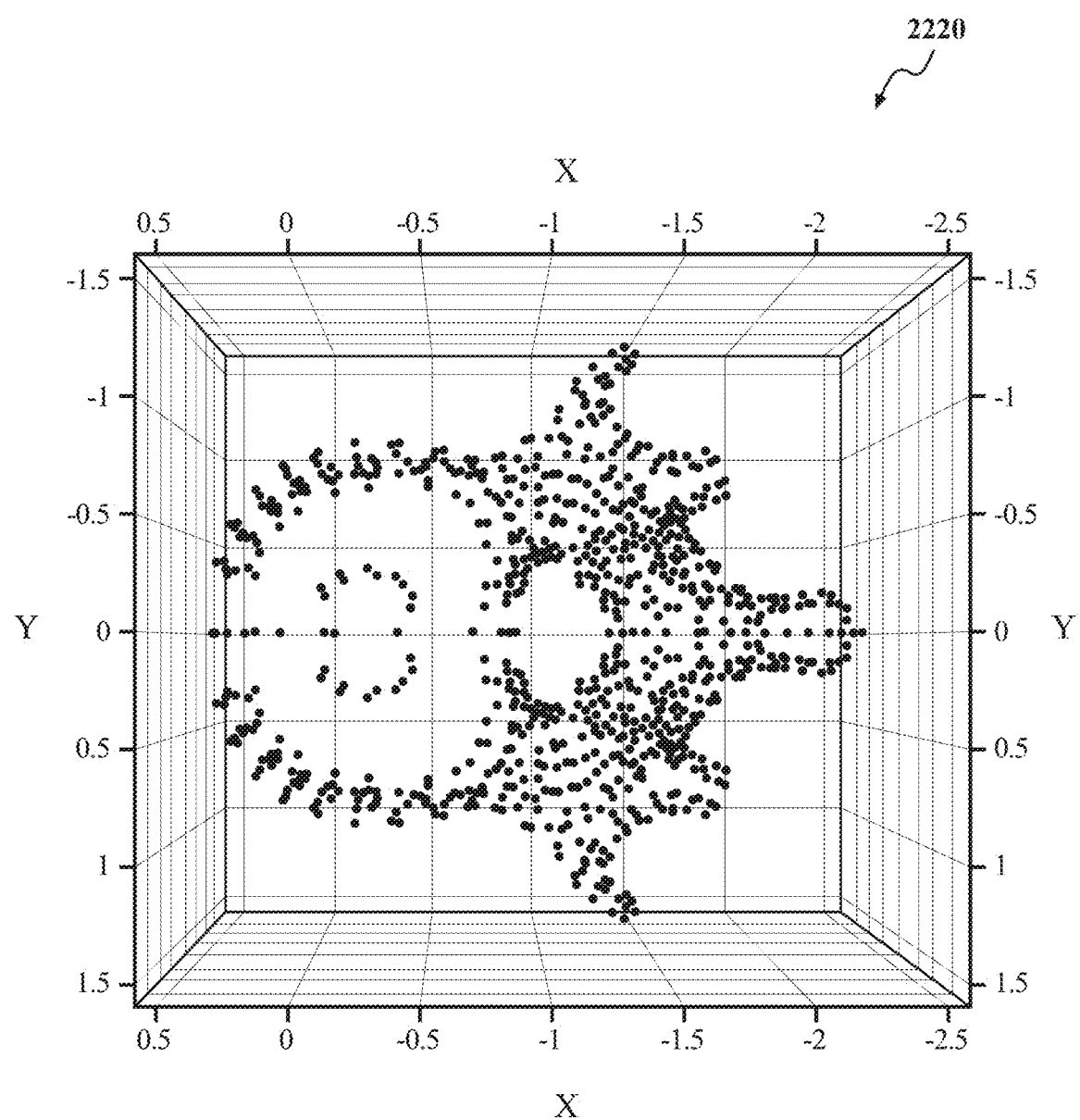
Figure 20C:
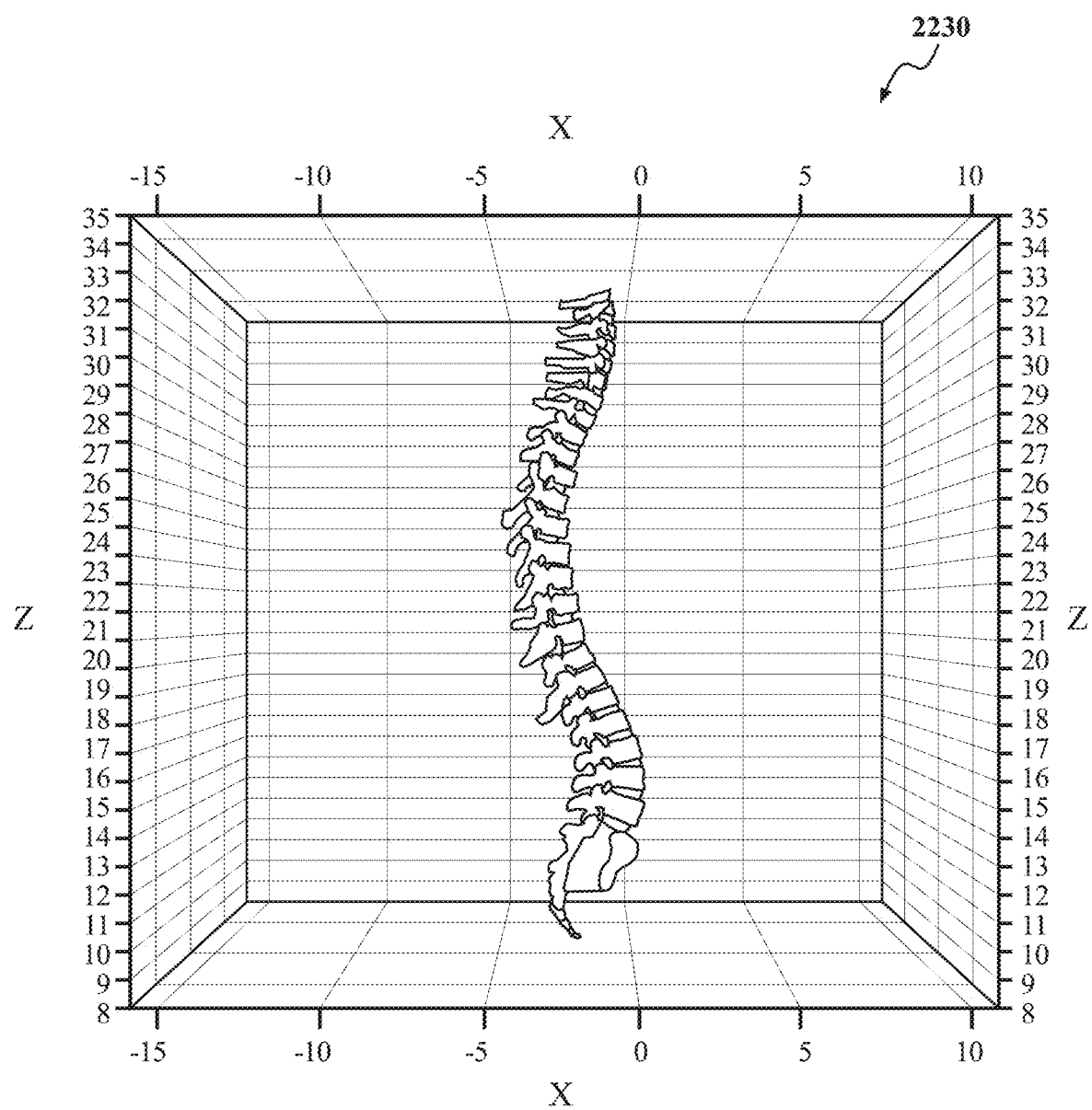
FIG. 20C is a three dimensional plot of a simulated spine comprising multiple vertebral body point maps in accordance with the disclosure.

FIG. 18 is a flow diagram illustrating in greater detail the process illustrated in block 1304 of FIG. 17. The process starts with multiple surface scans of the coronal and sagittal X-rays of a subject that produce approximately 1000 points for each vertebral body which point map module 2202 uses to create a point map of a vertebral body, similar to the point cloud map shown in FIGS. 20A-B, as illustrated by block 1402. The images in FIGS. 20A-B are the point cloud 2220 for vertebral body L4, with the sagittal view shown in FIG. 20A and axial view shown in FIG. 20B. Morphing module 2204 uses a point cloud model for each vertebral body and can generate a simulation of a patient's morphology in a point cloud for the entire spine, similar to spinal point cloud model 2230 as illustrated in the image of FIG. 20C. All or a portion or none of the spine simulation may be rendered with surfaces as described elsewhere herein.

Figure 21A:
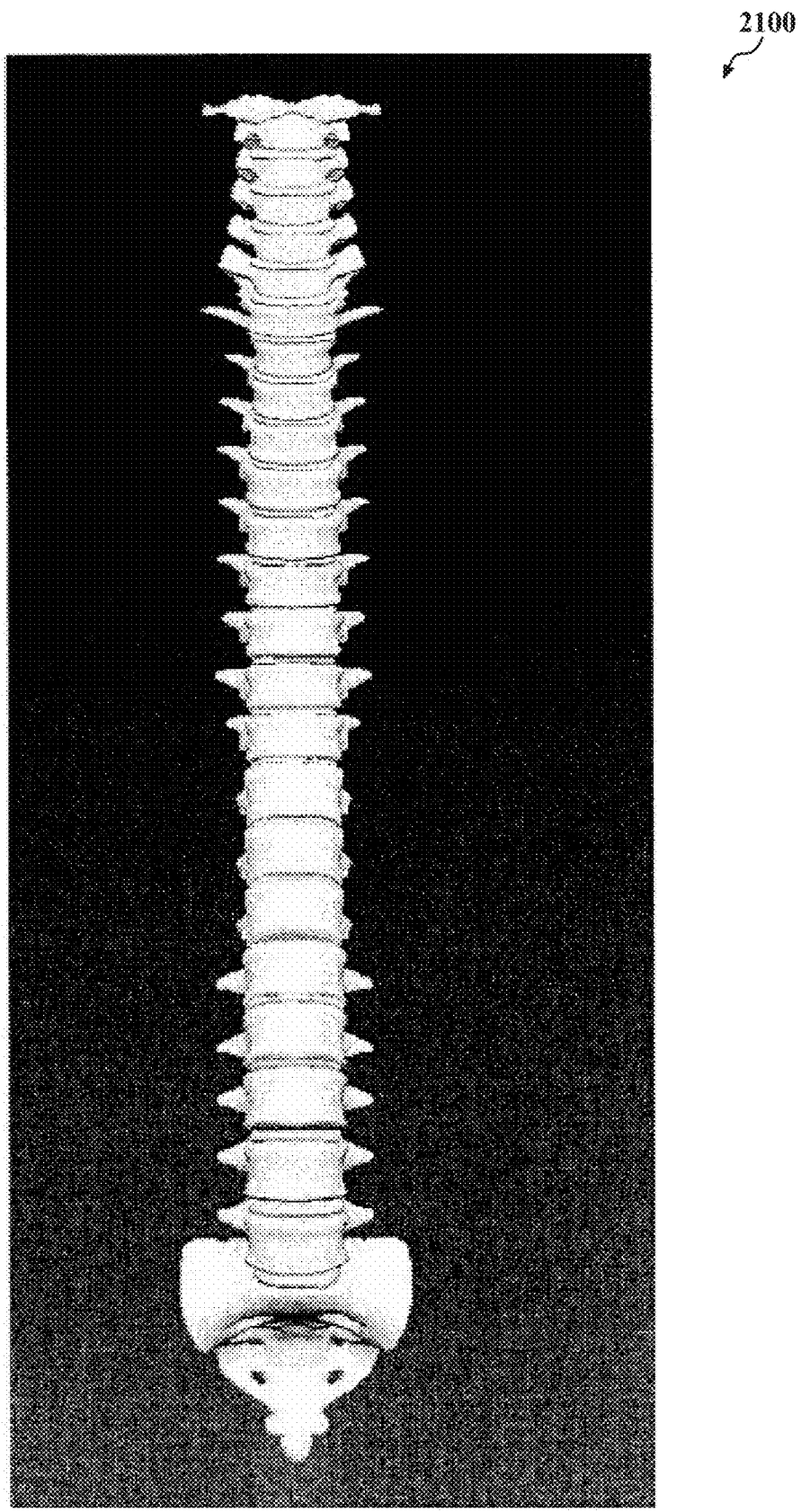
FIGS. 21A and 21B illustrate a spine model in the coronal and sagittal planes, respectively, with vertebral bodies that appear as if in a normal spine in accordance with the disclosure.
Figure 21B:
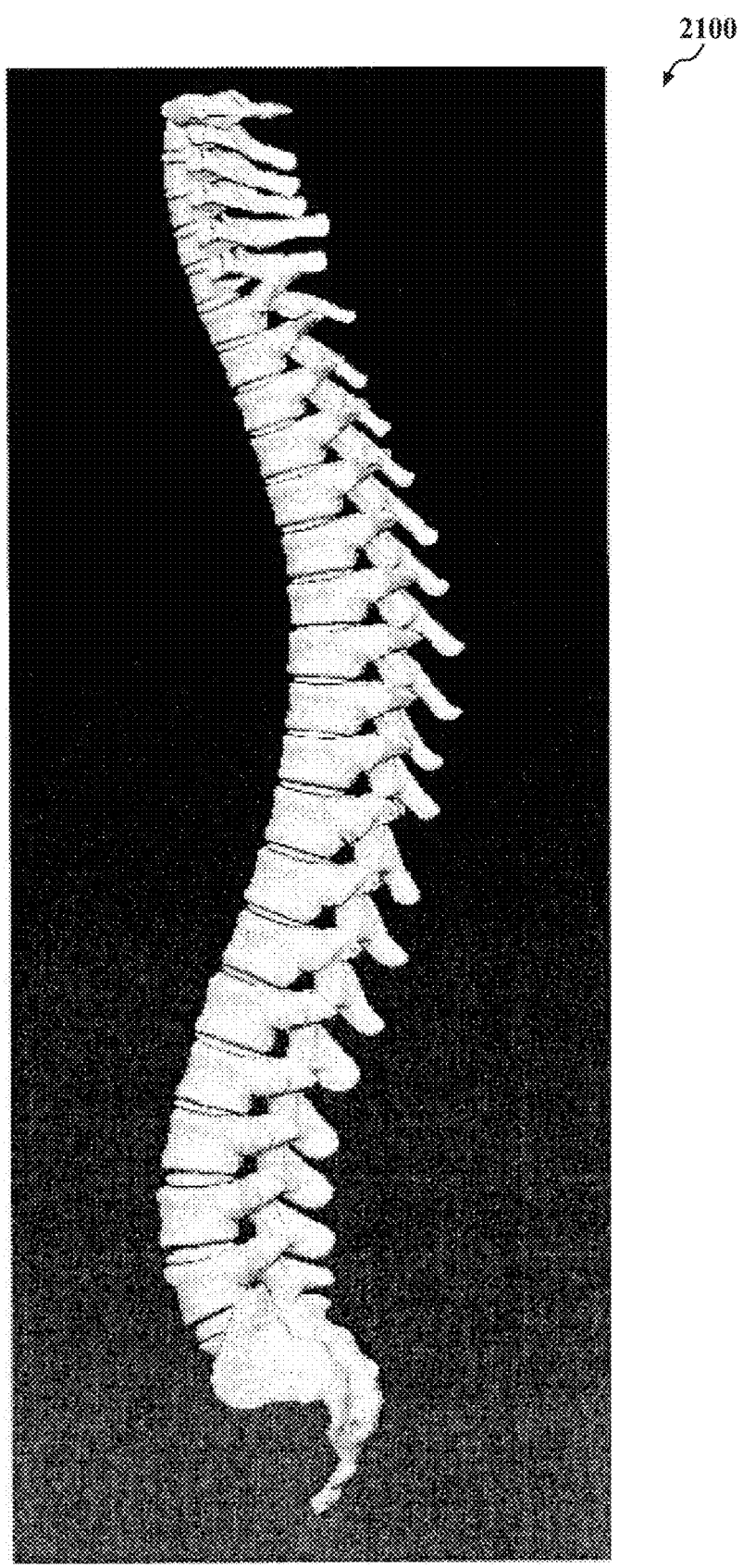
Figure 21C:
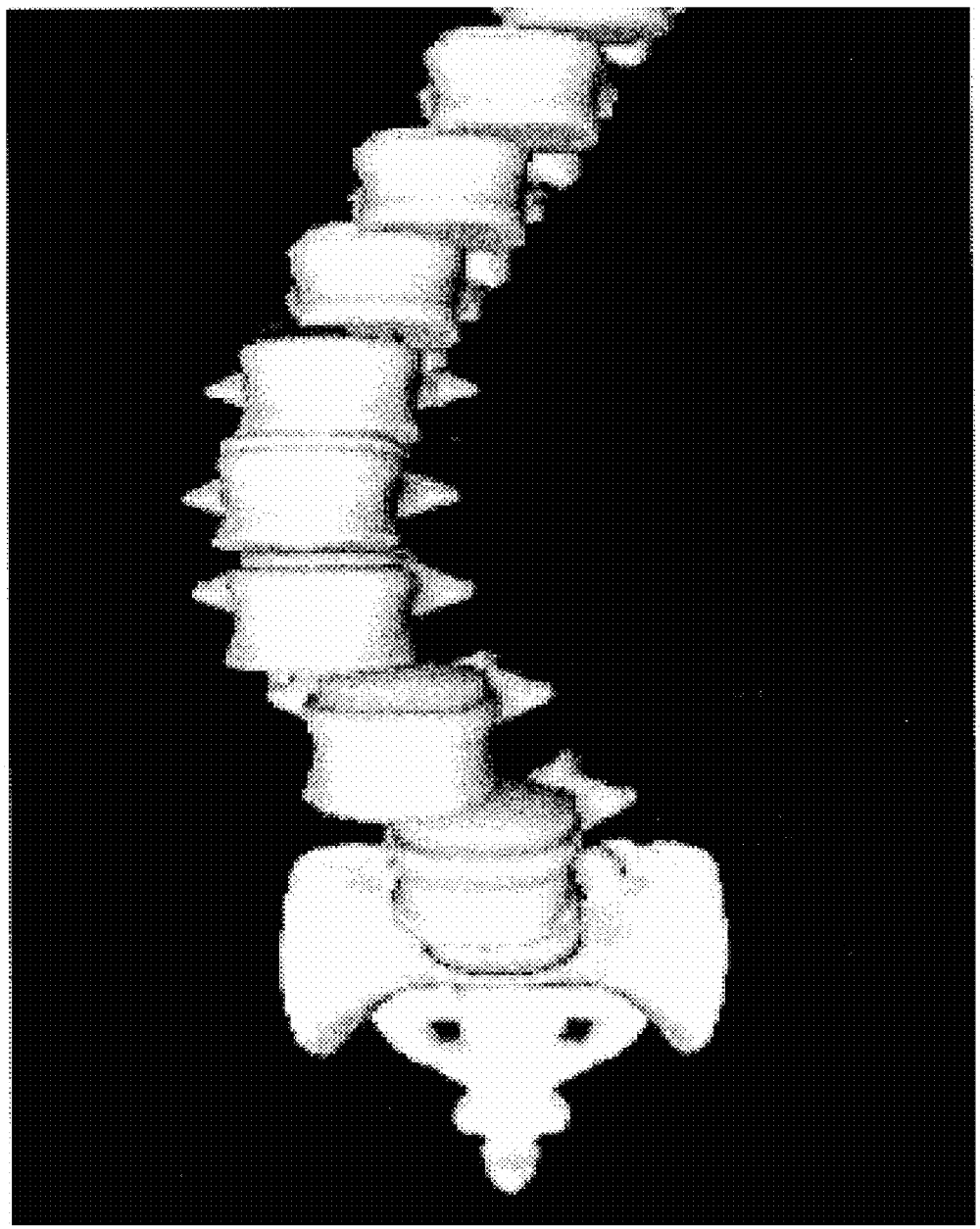
FIG. 21C illustrates a spatial translation of the vertebral bodies of the model spine of FIG. 7A in accordance with the disclosure.

Each point in a point cloud map may be connected to two or more other points to generate a face with vectors associated with such points and faces. The vectors describe the direction and displacement of the points in the point cloud model comprising the virtual vertebral body model. In one embodiment, morphing of the point cloud model to simulate an individual patient's actual deformity requires modifying those vectors. In one implementation, morphing module 2204 performs a translation of all of the points in a vertebral body point cloud model. From the output of point map module 2202, the X, Y, Z spatial coordinates of a central point on each of the vertebral bodies form a centerline that collectively comprises a curve representation in three-dimensional space describing the deformity of an individual's spine in three dimensions. Morphing module 2204 utilized the spatial coordinates output of module 202 and translates all the points in a vertebral body point cloud model in a given direction as determined by the output of point map module 2202. As such, a spine model, as illustrated in FIGS. 21A-B, has the points comprising in the respective vertebral body models thereof translated spatially according to corresponding points on the CVBL to simulate the arrangement of center points of the vertebral bodies along the CVBL, as illustrated by the image of FIG. 21C. However, translation alone of spatial coordinates will not necessarily yield a realistic simulation. In FIG. 21C, the center line of each VB is in the correct location on the CVBL but notice that the vertebral bodies have slid off of one another, a.k.a. subluxation, that does not realistically simulate the proper orientation of adjacent vertebral bodies relative to each other. This is because normal spines have a glue between the vertebral bodies, i.e. the disc, which prevents such sliding. In a real spine, instead of subluxation, adjacent vertebral bodies are angled and/or rotated due to the deformity of a patient's particular morphology. To prevent the inaccuracies created by subluxation using just a translation operation, the disclosed system and technique simulate actual movement of the vertebral bodies in the spinal column by utilizing a combination of translation, angular displacement and angular rotation of the respective vertebral bodies to simulate a patient morphology.

Figure 22A:
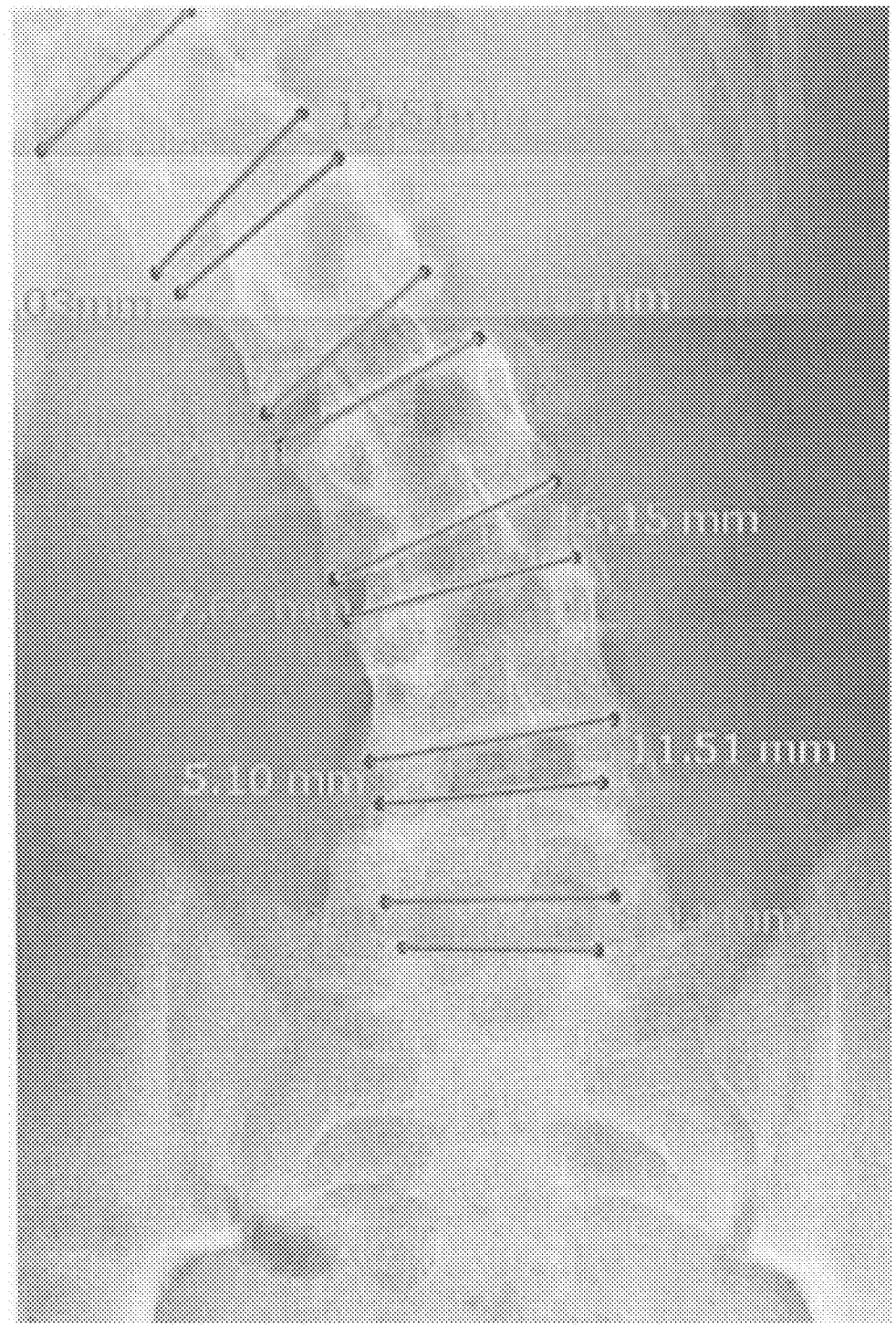
FIGS. 22A and 22B are X-ray images in the coronal and sagittal planes of the Lumbar spine, respectively, annotated with lines representing the discs and endplates of vertebral bodies in accordance with the disclosure.
Figure 22B:
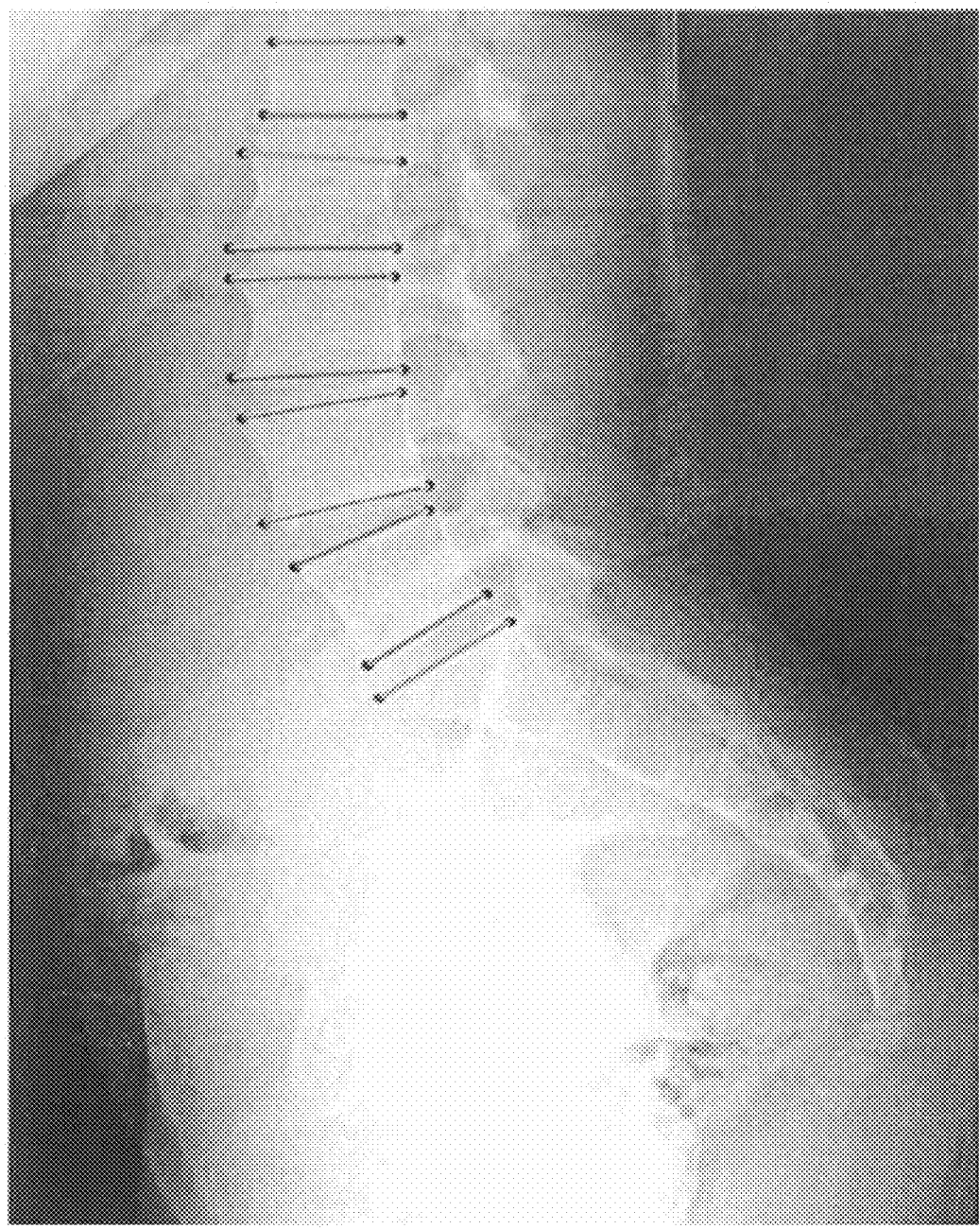

In one implementation, orientation module 2203 automatically identifies each disc and the endplates of the adjacent VBs in an image. Given this information, the length and height of each VB structure is calculated in both the sagittal and coronal planes. FIGS. 22A and 22B are X-ray images in the coronal and sagittal planes, respectively, annotated with lines representing the discs and endplates of vertebral bodies. In one embodiment, the end plates of vertebral bodies may be annotated in different colors. In one embodiment, orientation module 2203 may generate a user interface that enables a user to manually mark the end plates of vertebral bodies on an image. Orientation module 2203 may then calculate measurements of various marked features and store the results thereof.

According to one embodiment, a first method for rapid generation of a simulated patient morphology is illustrated in the flowchart of FIG. 18. In this method, the center of vertebral body S1 endplate is used as a reference pivot point by which each point in every point cloud model of a vertebral body is pivoted, translated, and rotated, and proportionally scaled, as necessary, relative to the reference pivot point. Referring to FIG. 18, after at least two different images in different planes normal to each other are obtained, and the CVBL generator 2201 processes the image data, calibrates the image data to establish a common frame of reference, and creates a Central Vertebral Body Line, as previously described, a model, e.g. a point map, of each vertebral body in a set of normal vertebral body models is retrieved, as illustrated at block 1402. In embodiments, the vertebral body models may be a generic normal set of vertebral bodies unrelated to the specific patient or, alternatively, the vertebral body models may be derived from the patient's medical image data, such as from CT scan data, or a combination of both. Next, the end plates or edges of the vertebral bodies of interest on one or both images are identified through either manual input, received through a user interface generated by module 2207, or by an automated detection algorithm executable by orientation module 2203, as illustrated by the images in FIGS. 22A-B. Specifically, orientation module 2203 determines the slope and midpoint of the vertebral body endplates in each of the sagittal and coronal planes for each vertebral body and then calculates the angulation vectors in each of the sagittal and coronal planes, as illustrated at block 1404. The orientation module 2203 then calculates the translation and tilt angles to the center point of each of the vertebral bodies, e.g. cervical, thoracic, lumbar, sagittal, and coronal, and the angular rotation vectors, and then translate all the points in the corresponding vertebral body point cloud model relative to their original coordinates, as illustrated at block 1406. Next, the morphing module 2204 pivots the point cloud models around the center point of vertebral body S1, as illustrated at block 1408. Note, once the pivot point and the x,y,z coordinates of the points in a point cloud model are known, the point cloud model can be morphed in any order, e.g. translated, rotated, and then angled, or, angled, rotated, and then translated, or in other procedural orders, etc., with the same result.

Finally, the simulation may be rendered on a display by rendering module 2206 and UI interface VR/AR module 2207, as illustrated at block 1410. Optionally, if it is desirable to see the simulated vertebral body in a solid surface rendered manner, the simulation may be all partially rendered with surface features.

Figure 23A:
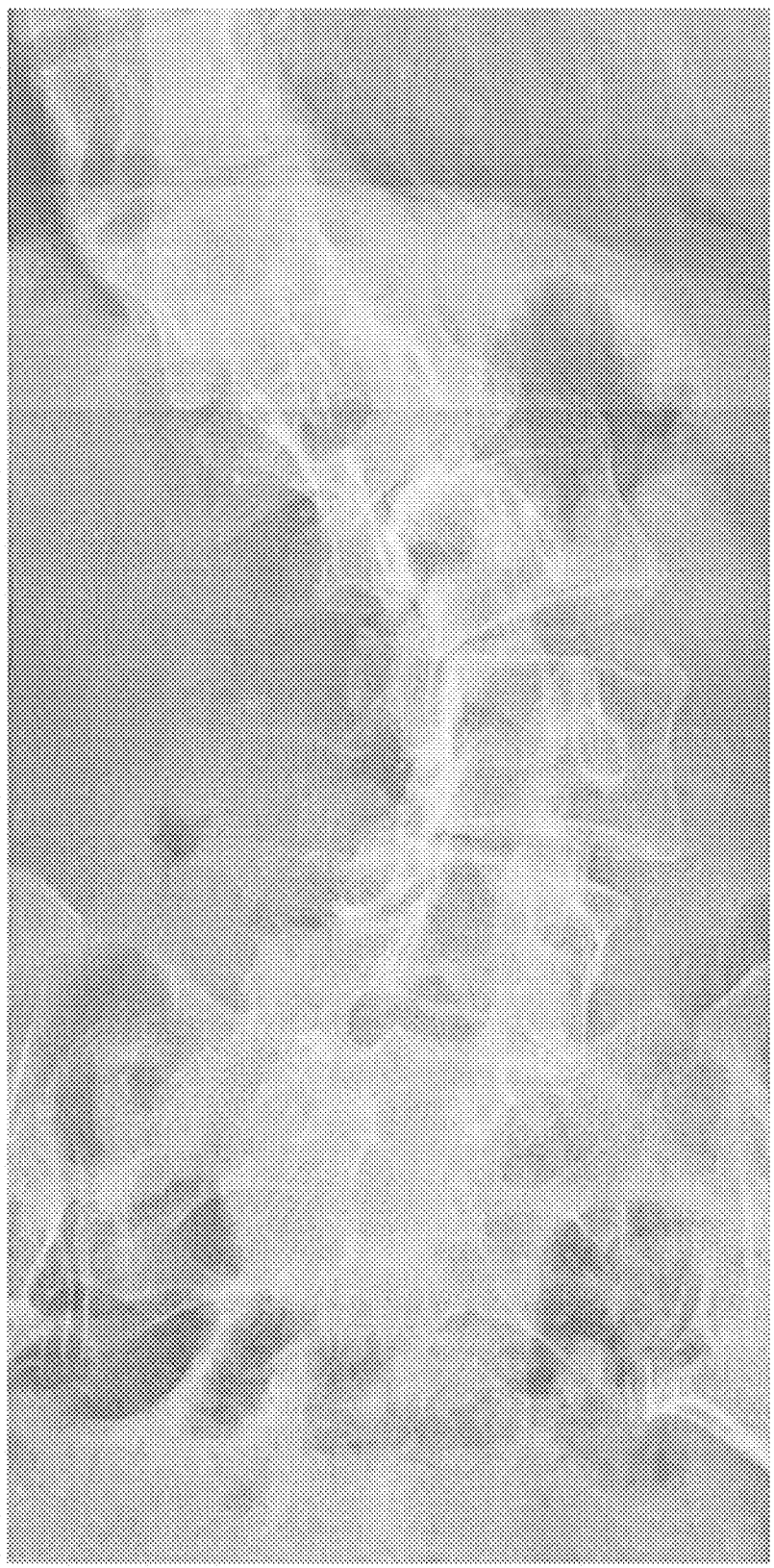
FIG. 23A is a patient coronal X-ray.
Figure 23B:
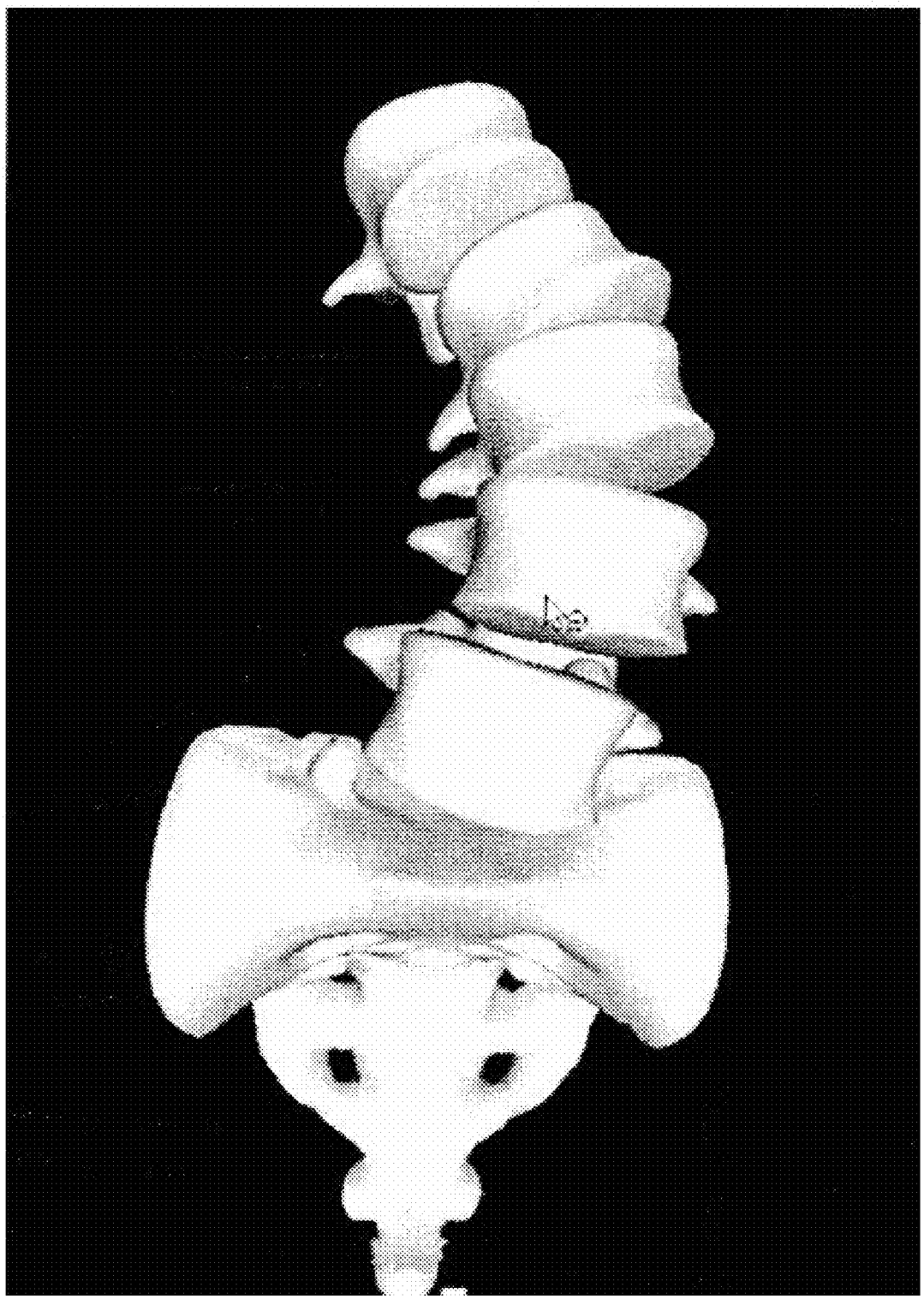
FIG. 23B is an image of a morphed simulated three-dimensional spine illustrated in the patient X-ray of FIG. 23A using the system and techniques described herein in accordance with the disclosure.

FIG. 23B is an image of a three-dimensional simulation 2300B of a morphed three-dimensional spine derived from the actual patient coronal X-ray of FIG. 23A using the systems and methods described herein. The above method can be used for any of the lumbar, thoracic and cervical spine simulations. For example, in the cervical spine, vertebral bodies C1 to T6 with the center of T6, the lowest vertebral body utilized, serving as the base pivot/translate point. Note, depending on which vertebral bodies are to be simulated, another point may be used as the base pivot/translate point about which the other point cloud models of vertebral bodies will be referenced. In simulation 2300B of FIG. 23B, vertebral bodies L3, L4 and L5 are morphed according to the morphology of the X-ray of FIG. 23A with L3 angulated and very close to touching L4 simulating the actual patient's morphology, as seen in the actual the X-ray of FIG. 23A. As mentioned above, the above described method can be used for any of Lumbar, Thoracic, or Cervical spine simulations.

Figure 23C:
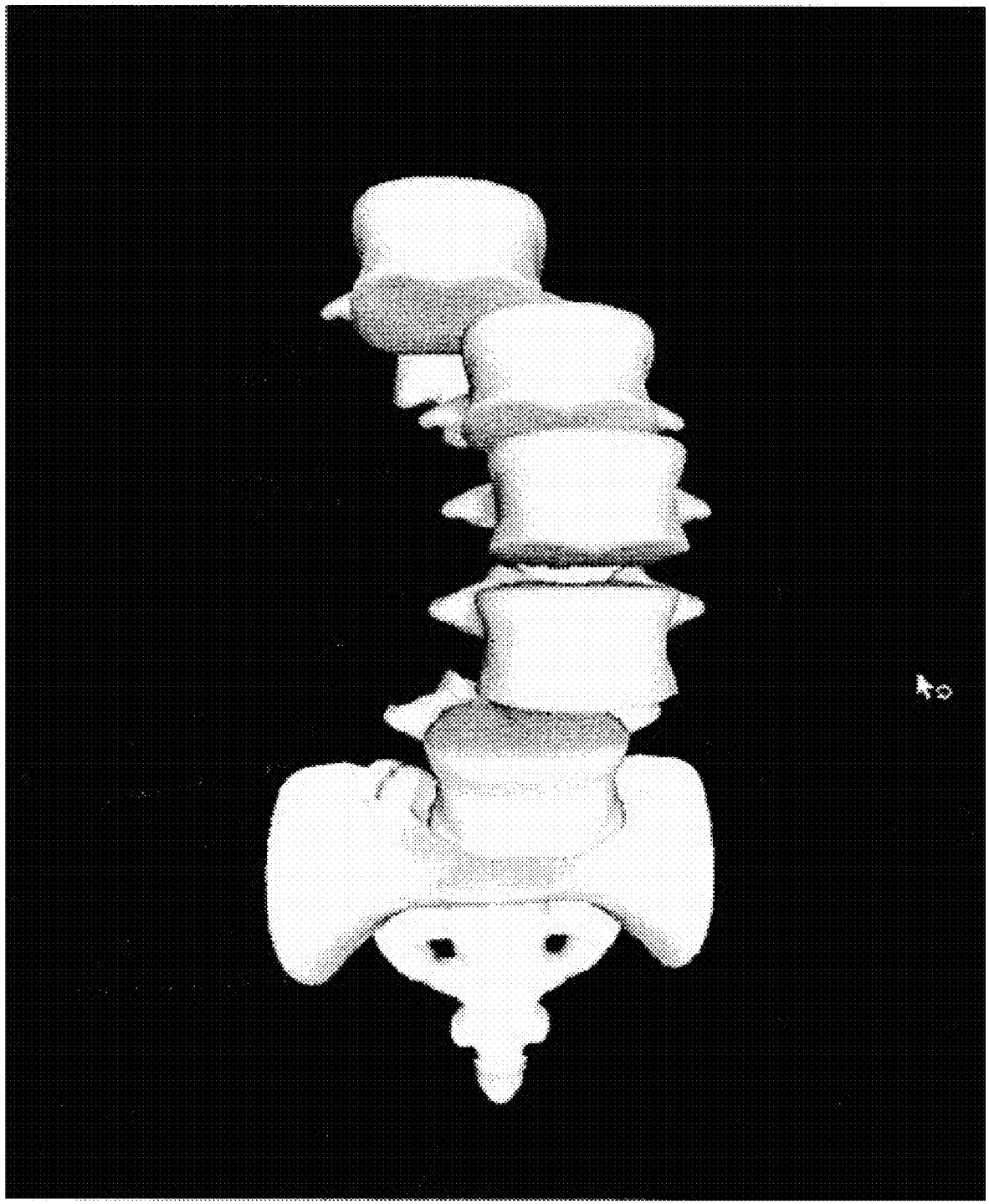
FIG. 23C is an image of a partially morphed simulated three-dimensional spine illustrated in the patient X-ray of FIG. 23A in accordance with the disclosure.
Figure 23D:
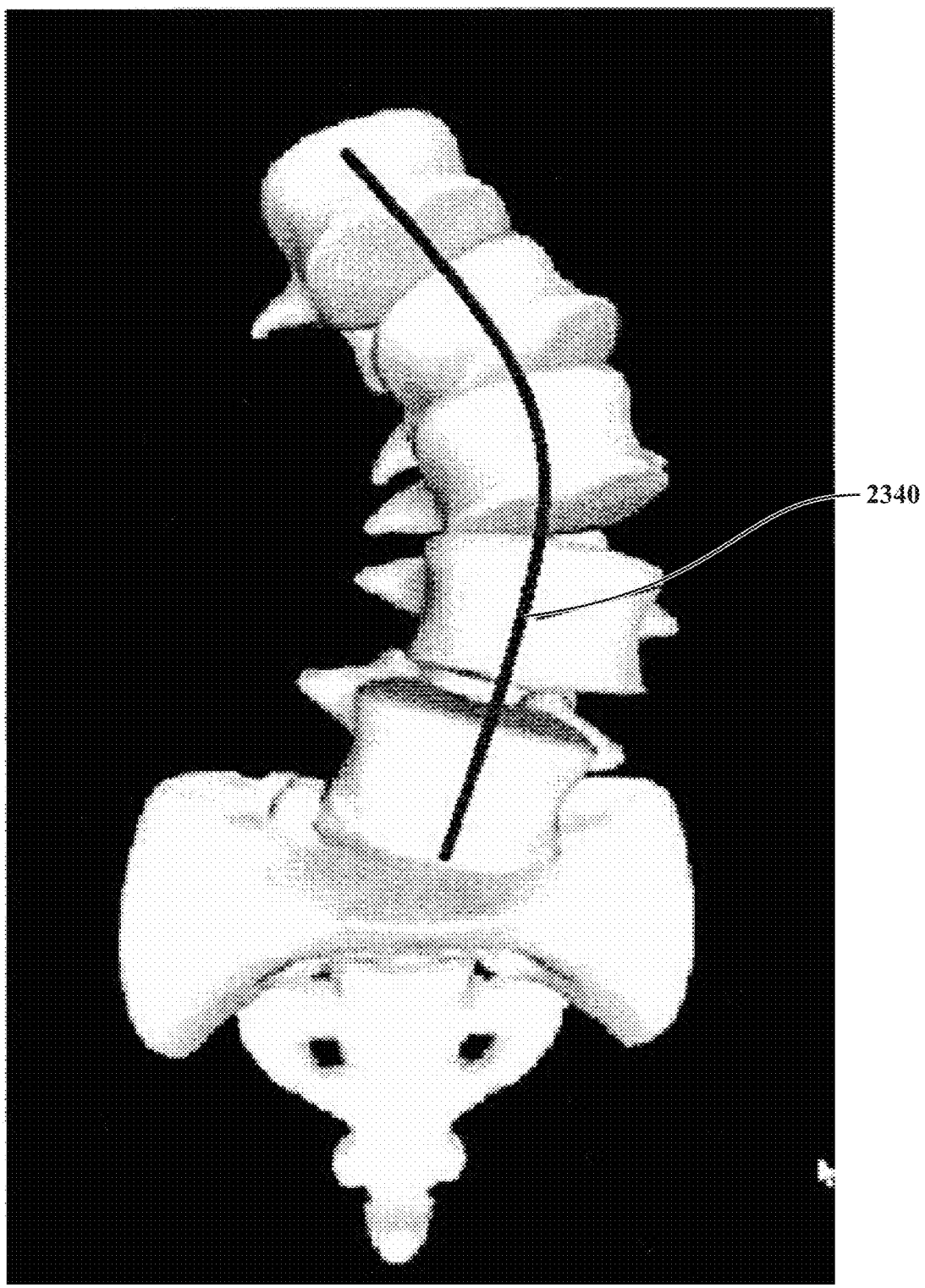
FIG. 23D is an image of a morphed simulated three-dimensional spine illustrated in the patient X-ray of FIG. 23A annotated with a line representing the CVBL in accordance with the disclosure.

FIG. 23C illustrates a simulation 2300C, in which only translation of each vertebral body center point was utilized without angulation or rotation of the respective vertebral bodies relative to a reference point, such simulation suffering from the effects of subluxation, similar to the simulation 2120 of FIG. 21C. FIG. 23D is an image of simulation 2300B, similar to that illustrated of FIG. 23B, but annotated with a line 2340 representing the CVBL about which the point cloud models of the vertebral bodies were translated pivoted and/or rotated to create the simulation 2300B.

According to another embodiment, a second method for rapid generation of a simulated patient morphology is disclosed and is a variant to the process illustrated in the flowchart of FIG. 18. In this second method, the left/right/front/back edge end points of each vertebral body of interest are identified by orientation module 2203 and a three-dimensional shape of each of the vertebral bodies is created. Because the shape, typically an irregular boxlike construct is defined by spatial coordinates, the dead center of each box may be determined, with the center point of a vertebral body box serving as a reference pivot point. Every other point in the point cloud model for that individual vertebral body may then be pivoted, angled, translated, and proportionally scaled relative to this reference pivot point, similar to the process described with respect to block 408. Because the data structure describing the three-dimensional shape or box of each of vertebral body inherently contains the respective spatial coordinates of the edges and corners of the box, rotation of the vertebral body relative to a reference point, such as the center point of vertebral body S1 or other reference point on the patient image, in the first described method, is not required.

In the two methods outlined above, the data determining how the point cloud model of a vertebral body will be rotated is determined differently. In the first method, the CVBL provides the translation data to move a vertebral body point cloud model to the correct spatial locations, and further provides the angulation data to tilt the vertebral body point cloud model so that its approximate center lies within the CVBL. In the first method, the reference point S1 is used to serve as the basis on which the rotation data, generated by measurement of the endplates and other characteristics of the vertebral bodies, is derived. Such rotation data is used to rotate the translated and tilted the vertebral body point cloud model into an orientation relative to the other VBs in a manner that more accurately simulates the patient's morphology. In the second method, the angulation data and the rotation data are determined by the center point of the vertebral body point cloud box which is initially assumed to lie on the CVBL, but, which after taking appropriate end plate and other measurements, may be determined to lie elsewhere. Once the center point of the vertebral body box is known, the appropriate translation scaling factors are used to tilt and appropriately rotate the points comprising the vertebral body point cloud model into appropriate orientation, without the need for an external reference point, such as S1, since the spatial coordinates describing the three-dimensional box of each of vertebral body inherently define the rotation of the VB relative to its respective center point.

In another embodiment, a third method is used for simulating spinal pathologies that are relatively simple deformities, such as Scheurmann's kyphosis, a Lenke 1A or a simple 5C. In this embodiment, all of the vectors associated with the point cloud of a VB are not calculated and morphed (translated, angled and rotated). Instead the central pivot point for each vertebral body, which happens to run through the CVBL, generated as previously described, is identified. Next, a number of pixels, e.g. 5, both above and below a pivot point on the CVBL are examined and the slope in both the sagittal and coronal planes calculated. In the illustrative embodiment, these 10 pixels are approximately 1 mm in length. The calculated angles are then applied to the point cloud model of a vertebral body and used to generate the image. This process is then repeated for each vertebral body of interest within the original images from which the simulation was derived.

With any of the simulation methods described herein, once a simulation is generated it may be stored in a data structure in memory. In one embodiment, morphing module 2204 generates two separate tables with the data describing the spacial coordinates and other information describing the simulation for not only the CVBL but also each point in the point cloud model of each of the vertebral bodies within the spine. Such data set can be provided to rendering module 2206 to recreate the three-dimensional reconstruction appears.

Figure 24C:
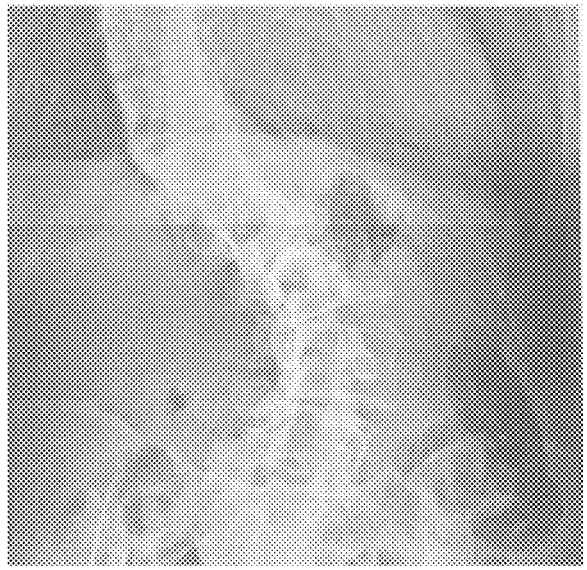
FIG. 24C illustrates the same patient coronal X-ray as FIG. 23A.
Figure 24D:
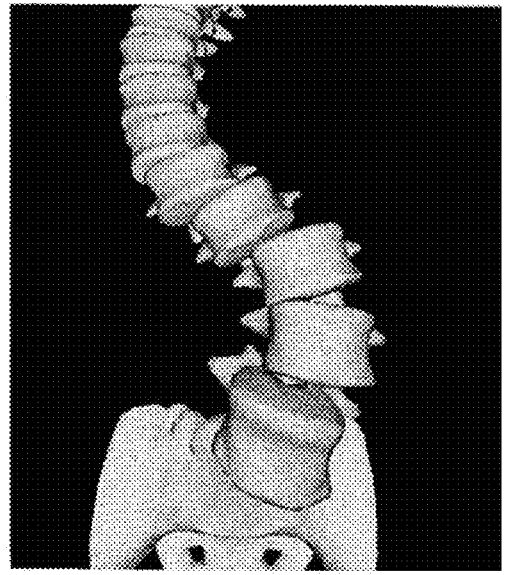
FIG. 24D illustrates a scaled three-dimensional simulation of FIG. 24B.

FIG. 24A illustrates a traditional three-dimensional reconstruction 2400A of the patient spine of FIG. 23A generated from CT scan data which required substantial computing resources to generate. FIG. 24B illustrates a morphed three-dimensional simulation 2402 of the patient spine image of FIG. 23A generated using the methods herein which were created in a matter of minutes. The three-dimensional simulation 2402 has been extended all the way up the spine with every vertebral body simulated and illustrated. Note, however, the vertebral bodies of simulation 2402 are smaller than the actual vertebral bodies in the CT scan reconstruction 2400 even though both recreations are in the same scale and in the same coordinate system. In order to add increased realism to the three-dimensional simulation 2402, the system described herein is capable of scaling the size of the individual vertebral bodies within the simulation 2402 by predetermined amounts or based on user defined input. Because each vertebral body in a simulation is modeled with a point cloud having a single, centrally located pivot point, such scaling entails expanding or contracting each vertebral body around the point cloud model central pivot point. Since the X, Y, Z coordinate of the central pivot point of a vertebral body is known and the three-dimensional distance to each of the points in the point cloud model of the vertebral body are also known, all points in the point cloud model associated with a vertebral body may be expanded (or contracted) with a proportional scaling factor. For example, to shrink a vertebral body in a simulation by 10%, the three-dimensional distance from the central pivot point of the vertebral body to a point in the vertebral body point cloud is multiplied by 0.9. To grow a vertebral body in a simulation by 25%, the three-dimensional distance as from the central pivot point of the vertebral body to a point in a vertebral body point cloud is multiplied by 1.25. Such scaling factor can be applied to any or all of the sagittal (x), coronal (y) or height (z) values of a vertebral body at once. All or selected vertebral bodies within a simulation can be scaled simultaneously. FIG. 24D illustrates a three-dimensional simulation 2404 of the patient's vertebral bodies which have been scaled in comparison to the unscaled simulation 2402 in FIG. 24B. Such scaling may be performed by an algorithmic process in rendering module 2206 in conjunction with module 2207 to enable interactive the scaling when the simulation image appears, e.g. the process queries through the user interface 2600, "Is this a good approximation?". If the user's answer is "no", the process may then receive user-defined input value, e.g. 12%, and then re-executes the proportional scaling of the simulation again as many times as necessary until the user is satisfied.

Within rendering module 2206 an algorithm creates a series of surfaces or faces among the points in the point cloud model describing a vertebral body, as illustrated by block 1404. Vectors normal to each point in the point cloud model and normal each polygon face are determined through a summation process relative to a hypothetical center point of the vertebral body, which hypothetical center point may lie within the Central Vertebral Body Line, and determine the orientation of the vertebral body in three dimensions, as illustrated in blocks 1408. This process is then repeated for all vertebral body models in the patient spine, in which the arrangement/morphing of each vertebral body, e.g. any of translation, angular displacement and angular rotation, may occur iteratively. A complete three-dimensional simulation based on just the point cloud models of all vertebral bodies may be completed iteratively, resulting in the simulation shown in FIG. 20C, prior to the three-dimensional simulation being, optionally, surface rendered, as indicated block 1410 to have the exterior surface appearance illustrated in FIG. 23B. FIG. 23B is an image of a morphed simulated three-dimensional spine derived from the actual patient coronal X-ray of FIG. 23A similar to that using the systems and techniques discussed herein. Such simulation of a patient spine may then be further morphed by the morphing module 2204 in response to a pre-determined percentage of correction as specified by a surgeon through the material module 2205, as illustrated by block 1414, as explained elsewhere herein.

In an illustrative embodiment, the curvature detection module 215 processes sagittal and coronal X-rays, although any image files or data format may be utilized, including DICOM images. The CVBL generator 2201 calibrates the image data to establish a common frame of reference and then creates a Central Vertebral Body Line. Curvature detection module 2215 either acquires or calculates the following variable values:

Patient ID
Timeframe
highest vertebra X
highest vertebra Y
highest vertebra Z
Head Over Pelvis Measures
X range
Y range
n rows
Mean X: $\Sigma(X)/n$
Mean Y: $\Sigma(Y)/n$
$\Sigma|X|/n$
$\Sigma|Y|/n$
SSx
SSy
variance X
variance Y
variance total
stdev X
stdev Y
lin dist HoP ideal
covariance (X,Y)
r(X,Y)
Angled Measures
/SSx/
/SSy/
/var X/
/var Y/
/var total/
/stdev X/
/stdev Y/
/covariance (X,Y)/
/r(X,Y)/

Particularly with Scoliosis patients, an important metric is Head-Over-the-Pelvis (HOP) measurement. The data generated by curvature detection module 2215 also forms the basis for other calculations including two nonlinear regression equations, (Sagittal vs Height and Coronal vs Height), r2 (coefficient of determination) point estimates, three-dimensional Plots, and three-dimensional measurements table.

In embodiments, the functionality of the curvature detection module 2215 may be partially implemented with a software application named Materialise 3Matic, commercially available from Materialise, Plymouth, Mich. that is intended for use for computer assisted design and manufacturing of medical exo- and endo-prostheses, patient specific medical and dental/orthodontic accessories and dental restorations. In embodiments, the functionality of the curvature detection module 2215 may be further partially implemented with a software application named Materialise Mimics, also commercially available from Materialise, Plymouth, Mich., which is an image processing system and preoperative software for simulating/evaluating surgical treatment options that uses images acquired from Computerized Tomography (CT) or Magnetic Resonance Imaging (MRI) scanners. The Materialise Mimics software is intended for use as a software interface and image segmentation system for the transfer of imaging information from a medical scanner such as a CT scanner or a Magnetic Resonance Imaging scanner to an output file.

According to another aspect of the disclosure, materials module 2205 enables the three-dimensional simulation of the patient specific morphology to predictively undergo preoperative mechanical testing. Material module 2205 is a preoperative planning tool that makes mechanical calculations and visually guides the surgeon through the process of choosing the correct hardware. Because curvature detection module 2215 generates a table or other data structure of three-dimensional spatial coordinates, e.g. X, Y, and Z, all of the equations of state in the fields of mechanical engineering, physics, mathematics and materials science are available, including the ability to determine and calculate stress/strain and fatigue in bone, or any implant materials, including CoCr, Ti-6Al-4V. When the positions of pedicle screws, rods, and interbodies are known, along with the materials from which such items are made, statistical analysis is possible enabling calculations like truss analysis, three and four point bend tests, and calculating the stress distribution at certain points.

In embodiments, materials module 2205 generates 2×24 array of data representing visual structures or icons of the posterior pedicles of the spine that are morphed with a patient's pre-op curve as generated by the curve detection module 2215 in a manner described herein. In one embodiment, the structures are geometric in shape. FIG. 26 is a screen shot of a user interface 2600 by which a surgeon enters various data through a series of either drop down menus or slider bars or dialog boxes to enter any patient specific parameters, including things like, location of pedicle screws, screw material, rod dimensions and materials, patient risk factors (smoker, drinker, BMI, etc.), age, height, curve stiffness, everything specific to that patient. These input data are then used in a series of appropriate algorithms within materials module 2205 perform the stress/strain calculations and rendering module 2206 generates a visual representation of the hardware with a color coding or other visual graphics indicating if acceptable levels of risk are associated with the designated hardware configuration The pedicle icons will then change to a simple red-yellow-green display indicating change (red), caution (yellow), acceptable (green). Other visual schemes it may be equivalently utilized. For example, if the patient is a 6'4" sedentary, male smoker and the surgeon selects 5.5 mm PS at L4-S1, the pedicles change to red. If size is changed to 6.5 and the pedicles may change to yellow (it is know from the literature that 6.5 screws in the lower lumbar spine fail 30% of the time and 30% is too high.) If the entered data instead related to a 5'6", 70 year old female, all mechanical calculations may be within in acceptable limits and the color indicators associated with each pedicle may change to green.

An accumulated human clinical database may provide a level of detail to look at how patients' spines deform for every given morphology and enables the use of predictive analytics for outcomes, including any of 30 day hospital readmission, PJK, QoL scores, revision surgery, etc.

Figure 25A:
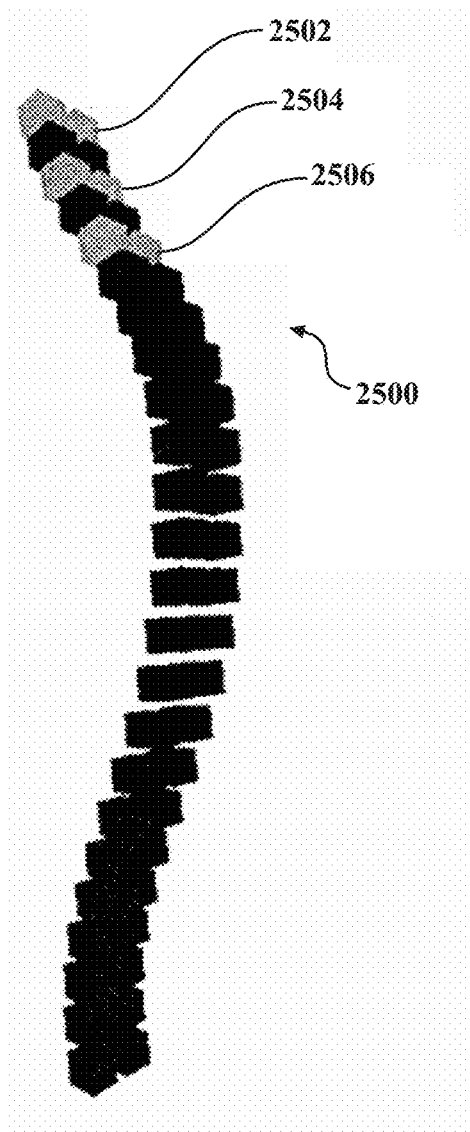
FIG. 25A illustrates conceptually a 2×24 array pedicle model of a patient spine morphed in three dimensions and rotated to show partial sagittal and coronal views in accordance with the disclosure.
Figure 25B:
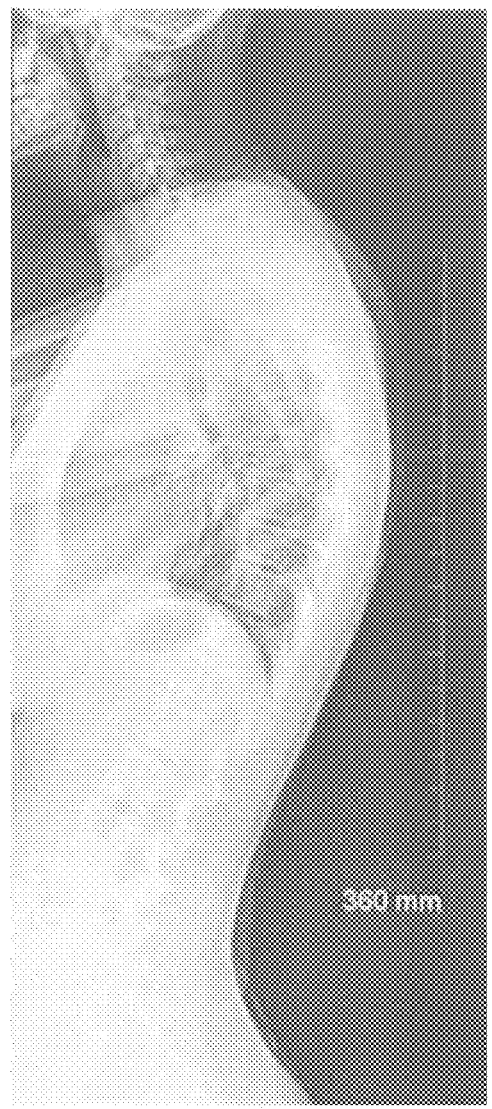
FIG. 25B is the actual patient sagittal X-ray from which the morphed simulated three-dimensional spine illustrated in FIG. 10A was derived in accordance with the disclosure.

FIG. 25A illustrates conceptually the 2×24 pedicle model array 2500 of a patient spine morphed in three dimensions and rotated to show partial sagittal and coronal views in which the pedicle pairs 2502, 2504 and 2506, representing C1, C3 and C5, respectively, have been colored or designated with some other visual indicator. FIG. 25B is a sagittal X-ray of the patient from which the simulation was derived, in further consideration of the input parameters illustrated in the screen shot of the user interface 2600 generated by module 2207, as illustrated in FIG. 26. In this embodiment, the visual representation of the anatomical structure, e.g. the posterior pedicles, may be any geometric shape or other visually discernible indicator, the purpose of which is to be arranged to simulate the approximate location thereof without the need for the exact details of the structure as described in the other processes disclosed herein.

Material module 2205 enables stress calculations, surgical pre-operative planning and predictive analytics. For the patient data utilized in FIGS. 9 and 10, the patient's head weighs about 12 lbs and the head is 10.5" out of top dead center, so the head adds an extra 122 in-lb of torque to the construct (Moment=Force×Distance; Moment=12 lbs×10.5"=122 in-lbs). With this information the surgeon may more accurately choose the appropriate hardware capable of postoperatively achieving the desired percentage of correction of the patient's specific morphology.

The disclosed system and techniques enables the ability to morph simulations of spines, both two-dimensional and three-dimensional, in any increment, e.g. 10% intervals, 5% intervals, 0.1% intervals. Knowing how much to move/morph the spine increases the predictive analytics capabilities and, therefore, the likelihood of success of a procedure. Because the disclosed system enables calculations in three-dimensional space, any of the previously listed variable parameters may be manipulated.

In embodiments, the rendering module 2206 and interface module 2207 creates a visual image of the three-dimensional simulation that illustrates how the patient may look after surgery that may include an outline of the skin (shoulder imbalance, rib hump, thoracic kyphosis, etc.) in a pre-operative condition and morphing the simulation into the post-op positions. In embodiments, the rendering module 2207 utilizes two white light photographs (or X-rays if they include the patient's skin), one sagittal and one coronal to achieve such rendering.

A portable spine application which may be part of the user interface module 2207 converts the three-dimensional simulation model rendered by module 2206 and converts the simulation into a virtual reality (VR)/augmented reality (AR) format, using any number of commercially available applications, which is then made available to the surgeon on his/her phone or other portable device 15, as well as the patient on their portable device 17. For example, given the three-dimensional simulation of the patient morphology, module 2207 may generate an VR/AR overlay in either the supine position while lying on the table, prepped for surgery to enable the surgeon to visualize the procedure in real time, or the final post-operative configuration. For patients with flexible spines, a standing X-ray looks nothing like the supine position. The disclosed system and techniques enables the morphing of the patient spine in two-dimensional and three-dimensional simulations and have simulation over-layed with surgeon vision using either Virtual or Augmented Reality.

Although the illustrative embodiments utilize X-ray images, other image formats may be utilized with the disclosed system and techniques. In embodiments, the disclosed system and techniques may be used with DICOM data. Digital Imaging and Communications in Medicine (DICOM) is a standard for storing and transmitting medical images enabling the integration of medical imaging devices such as scanners, servers, workstations, printers, network hardware, and picture archiving and communication systems (PACS) from multiple manufacturers. DICOM images, including CT scans and MRI images, are typically three-dimensional and, using the techniques described herein, enable physics and mathematics to be applied to the modeled entities to gain more realistic models and simulations of the spine. Metrics such as areas, volumes, moment of Inertia for cubes, prisms, cylinders, and even internal organs may be calculable.

In an illustrative implementation, using only typical Sagittal and Coronal X-rays with the system and techniques described herein, a simulation of the patient specific (deformed) spine was created in three-dimensional in less than 1.5 minutes. The disclosed system and techniques can show the surgeon and patient a simulation of what the spine currently looks like and what it may look like after surgery.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto. While the illustrative embodiments disclosed herein have been described primarily with reference to the bony vertebral bodies within the spine, it should be understood that the disc structures between the bony vertebral bodies within the spine may also be modeled and morphed in a manner similar to that describes herein. In addition, other structures within the skeleton system such as shoulders, ribs, arms, hand, leg, or foot, etc., as well as other non-bony structures within the anatomy of a subject, may similarly be modeled and morphed utilizing the system and techniques disclosed herein.

What is claimed is:

1. A method, comprising:
    obtaining a first X-ray image of at least a portion of a spine of a target patient in a first plane;
    obtaining a second X-ray image of the at least a portion of the spine of the target patient in a second plane;
    drawing a line through vertebral bodies of the at least a portion of the spine of the target patient in the first X-ray image and in the second X-ray image;
    constructing a three-dimensional model associated with the target patient based on the lines drawn on the first and second X-ray images;
    acquiring medical data associated with a reference patient different from the target patient;
    predicting, based on the three-dimensional model associated with the target patient in view of the medical data associated with the reference patient, postoperative changes to movement of the spine of the target patient over time; and
    determining parameters of a spinal device based on the predicted postoperative changes to movement of the spine of the target patient.

2. The method of claim 1, wherein the parameters of the spinal device are determined based on predicted postoperative changes which include: a first predicted postoperative change to movement of the spine of the target patient at a first time, and one or more additional predicted postoperative changes at times subsequent to the first time.

3. The method of claim 1, wherein the spinal device is a screw, a rod, a cervical plate, a spine implant, an interbody device, or an artificial disc.

4. The method of claim 1, wherein the first plane is a coronal plane and the second plane is a sagittal plane.

5. The method of claim 1, further comprising obtaining a third X-ray image of the at least a portion of the spine of the target patient in an axial plane.

6. The method of claim 5, wherein constructing the three-dimensional model associated with the target patient includes constructing the three-dimensional model associated with the target patient based on the lines drawn on the first, second, and third X-ray images.

7. The method of claim 1, wherein the method further comprises:
    identifying a line on the first X-ray image; and
    identifying a line on the second X-ray image.

8. The method of claim 7, wherein the line on the first X-ray image and the line on the second X-ray image are colored lines and identifying the colored lines includes quantifying the color of the colored lines and identifying differences in characteristics of the colored lines;
    wherein the color of the colored lines includes at least one of red, green, or blue; and
    wherein the characteristics include at least one of intensity, hue, saturation, contrast, or brightness.

9. The method of claim 1, further comprising calibrating the first X-ray image and the second X-ray image.

10. The method of claim 1, further comprising:
    obtaining coronal Y-Z coordinates or pixels of a central vertebral line with vertebral bodies and discs identified; and
    obtaining sagittal X-Z coordinates or pixels.

11. The method of claim 1, further comprising compensating for differences in magnification between the first X-ray image and the second X-ray image.

12. The method of claim 11, further comprising scaling the first and second X-ray images.

13. The method of claim 1, further comprising combining the first X-ray image and the second X-ray image to construct the three-dimensional model associated with the target patient.

14. The method of claim 1, further comprising evaluating spines of a plurality of different reference patients for similarities to the spine of the target patient.

15. The method of claim 1, further comprising comparing medical data of the target patient with medical data of a plurality of different reference patients.

16. The method of claim 1, wherein acquiring the medical data associated with the reference patient different from the target patient includes obtaining a plurality of different four-dimensional models of spines.

17. The method of claim 16, further comprising:
    generating a respective score for each of the plurality of different four-dimensional models of spines based on a comparison to the three-dimensional model associated with the target patient; and
    comparing the respective scores against a predetermined score to predict movement of the spine of the target patient.

18. The method of claim 17, further comprising generating a consolidated four-dimensional model from the plurality of different four-dimensional models of spines with respective scores greater than the predetermined score to predict movement of the spine of the target patient.

19. The method of claim 1, wherein acquiring the medical data associated with the reference patient different from the target patient includes obtaining at least one four-dimensional model for a similar spine of the reference patient.

20. The method of claim 19, further comprising:
    analyzing the three-dimensional model associated with the target patient based on the at least one four-dimensional model for the similar spine of the reference patient to predict movement of the spine of the target patient; and
    determining the parameters of the spinal device based on the predicted movement of the spine of the target patient.

21. The method of claim 20, wherein the similar spine of the reference patient is an abnormal spine; and wherein the spine of the target patient is a one-level degenerative disc case and the similar spine of the reference patient is a two-level degenerative disc case.

22. The method of claim 1, wherein the medical data associated with the reference patient includes at least one of diagnosis information, operative information, follow-up information, quality of life score, cardia information, diabetes information, radiographic information, or intra-operative information.

23. The method of claim 22, wherein the quality of life score is selected from the group consisting of Visual Analog Scale (VAS), Oswestry Disability Index (ODI), Neck Disability Index, Rowland-Morris, Short Form Health Survey-12, Short Form Health Survey-36, Scoliosis Research Society-36 (SRS36), and Scoliosis Research Society-22 (SRS-22).

24. The method of claim 1, further comprising generating instructions to construct the spinal device with a three-dimensional printer based on the parameters of the spinal device.

* * * * *